(12) United States Patent
MacMillan

(10) Patent No.: US 6,784,323 B2
(45) Date of Patent: Aug. 31, 2004

(54) ENANTIOSELECTIVE TRANSFORMATION OF α,β-UNSATURATED ALDEHYDES USING CHIRAL ORGANIC CATALYSTS

(75) Inventor: David W. C. MacMillan, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 10/187,635

(22) Filed: Jul. 1, 2002

(65) Prior Publication Data

US 2003/0109718 A1 Jun. 12, 2003

Related U.S. Application Data

(60) Provisional application No. 60/338,451, filed on Dec. 5, 2001, provisional application No. 60/338,172, filed on Dec. 5, 2001, and provisional application No. 60/301,875, filed on Jun. 29, 2001.

(51) Int. Cl.[7] .................... C07C 45/00; C07D 233/28
(52) U.S. Cl. ................ 568/459; 568/467; 548/316.4
(58) Field of Search ............................. 568/459, 467; 548/316.4

(56) References Cited

U.S. PATENT DOCUMENTS

| | | |
|---|---|---|
| 6,307,057 B1 | 10/2001 | MacMillan et al. |
| 6,369,243 B1 | 4/2002 | MacMillan et al. |

FOREIGN PATENT DOCUMENTS

| | | |
|---|---|---|
| WO | WO 92/02505 | 2/1992 |

OTHER PUBLICATIONS

Ahrendt et al. (2000), "New Strategies for Organic Catalysis: The First Highly Enantioselective Organocatalytic Diels—Alder Reaction," *J. Am. Chem. Soc.* 122(17):4243–4244.
Evans et al. (1997), "Chiral $C_2$–Symmetric Cu(II) Complexes as Catalysts for Enantioselective Intramolecular Diels– Alder Reactions. Asymmetric Synthesis of (–)–Isopulo'upone," *J. Org. Chem.* 62(4):786–787.
Frederickson (1997), "Opitcally Active Isoxazolidines via Asymmetric Cycloaddition Reactions of Nitrons with Alkenes: Applications in Organic Synthesis," *Tetrahedron* 53(2):403–425.
Ishihara et al. (1996), "A New Powerful and Practical BLA Catalyst for Highly Enantioselective Diels–Alder Reations: An Extreme Acceleration of Reaction Rate by Brønsted Acid,"*J. Am. Chem. Soc.* 118(12):3049–3050.
Iwasawa et al. (1989), "Asymmetric Intramolecular Diels–Alder Reaction Catalyzed by the Chiral Titanium Reagent," *Chemistry Letters*, pp. 1947–1950.
Jen et al. (2000), "New Strategies for Organic Catalysis: The First Enantioselective Organocatalytic 1,3–Dipolar Cycloaddition," *J. Am. Chem. Soc.* 122(40):9874–9875.

Jensen et al. (2001), "Catalytic Asymmetric Friedel–Crafts Alkylation of β,γ–Unsaturated α–Ketoesters: Enantioselective Addition of Aromatic C–H Bonds to Alkenes," *Angew. Chem. Int. Edit.* 40(1):160–163.
Johannsen (1999), "An Enantioselective Synthesis of Heteroaromatic N–Tosyl α–Amino Acids," *Chem. Commun.*, pp. 2233–2234.
Maruoka et al. (1994), "Virtually Complete Blocking of α,β–Unsaturated Aldehyde Carbonyls by Complexation with Aluminum Tris(2,6–diphenylphenoxide)," *J. Am. Chem. Soc.* 116(9):4131–4132.
Ohta et al. (1996), "Novel 5–Hydroxytryptamine (5–$HT_3$) Receptor Antagonists. III. Pharmacological Evaluations and Molecular Modeling Studies of Optically Active 4,5,6, 7–Tetrahydro–1H–Benzimidazole Derivatives," *Chem. Pharm. Bull.* 44(9):1707–1716.
Paras et al. (2001), "New Strategies in Organic Catalysis: The First Enantioselective Organocatalytic Friedel–Crafts Alkylation," *J. Am. Chem. Soc.* 123(18):4370–4371.
Shi et al. (1995), "Synthesis of Axially Dissymmetric Chiral Ammonium Salts by Quaternization of Secondary Amines with (R)–(+)–2,2'–Bis(bromomethyl)–6,6'–dinitrobiphenyl and (R)–(+)–2,2'–Bis(bromomethyl)–1,1'–binaphthyl and an Examination of Their Abilities as Chiral Phase–Transfer Catalysts," *J. Chem. Research (S)*, pp. 46–47 (*J. Chem. Research (M)*, pp. 0401–0411).
Yang et al. (1998), "Design and Synthesis of Chiral Ketones for Catalytic Asymmetric Epoxidation of Unfunctionalized Olefins," *J. Am. Chem. Soc.* 120(24):5943–5952.

*Primary Examiner*—Johann Richter
*Assistant Examiner*—Sikarl A. Witherspoon
(74) *Attorney, Agent, or Firm*—Dianne E. Reed; Mark L. Warzel; Reed & Eberle LLP

(57) ABSTRACT

Nonmetallic organic catalysts are provided that facilitate the enantioselective reaction of α,β-unsaturated aldehydes. The catalysts are chiral imidazolidinone compounds having the structure of formula (IIA) or (IIB)

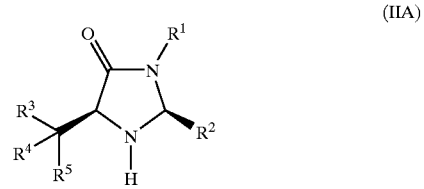

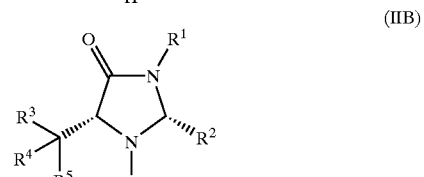

Figure 1A:
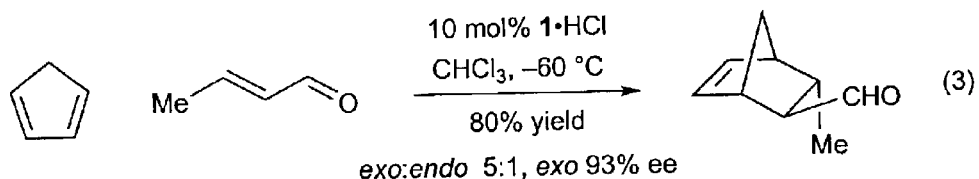
Figure 1A:
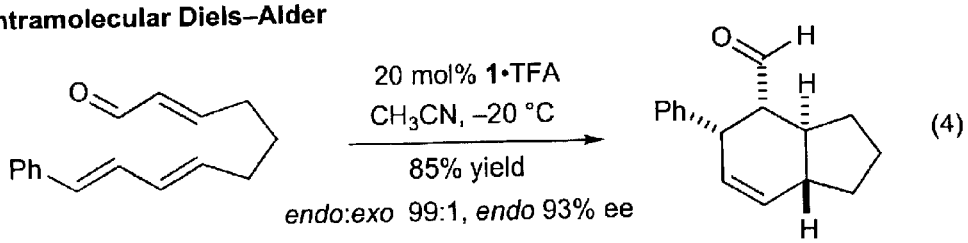
Figure 1A:
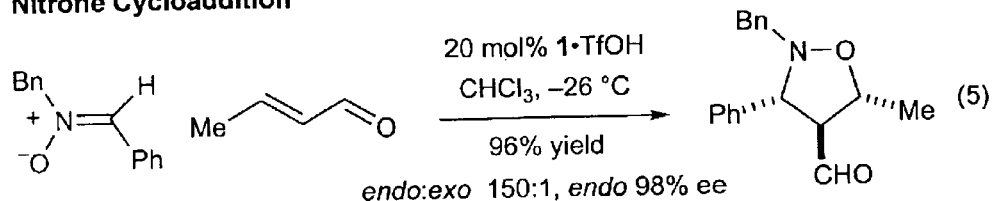
Figure 1A:
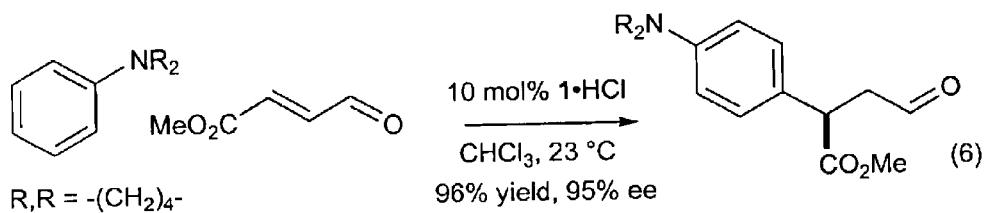
Figure 1A:
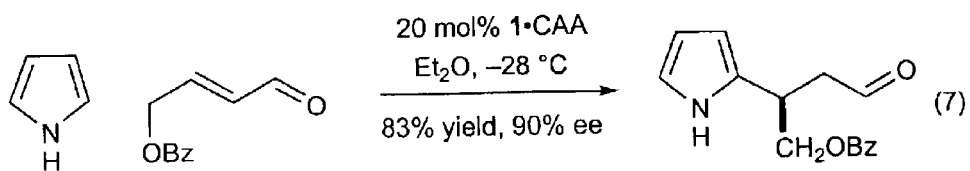

or are acid addition salts thereof, wherein, in one preferred embodiment, $R^1$ is $C_1$–$C_6$ alkyl, $R^2$ is tri($C_1$–$C_6$ alkyl)-substituted methyl, $R^3$ and $R^4$ are hydrogen, and $R^5$ is phenyl optionally substituted with 1 or 2 substituents selected from the group consisting of halo, hydroxyl, and $C_1$–$C_6$ alkyl. The chiral imidazolidinones are useful in catalyzing a wide variety of reactions, including cycloaddition reactions, Friedel-Crafts alkylation reactions, and Michael additions.

35 Claims, 6 Drawing Sheets

Diels–Alder

Intramolecular Diels–Alder

Nitrone Cycloaddition

Friedel–Crafts

Pyrrole Alkylation

Indole Alkylation

(8)

Furan and Thiophene Alkylation

(9)

Vinylogous Michael

(10)

Mukaiyama–Michael

(11)

Michael Addition

(12)

Amauromine
Takase *Tetrahedron Lett.* 1985, 847
Danishefsky *JACS* 1999, *121*, 11954

Fructigenine C
*J. Nat Prod* 1998, *61*, 804

Flustramine B
*J. Org. Chem* 1980, *49*, 1586

(1) Quaternary sterocenter(s)
(2) Vicinal sterocenter control
(3) Pyrroloindoline ring system
(4) Enantioselective Catalysis (−) Chimonanthine
Overman
*JACS* 1999, *121*, 7702

Urochordamine A
isolation
*Tetrahedron Lett.* 1993, 4819

ENANTIOSELECTIVE TRANSFORMATION OF α,β-UNSATURATED ALDEHYDES USING CHIRAL ORGANIC CATALYSTS

CROSS-REFERENCE TO RELATED APPLICATIONS

This application claims priority under 35 U.S.C. §119(e)(1) to the following provisional U.S. patent applications: Serial No. 60/301,875, filed Jun. 29, 2001; Serial No. 60/338,451, filed Dec. 5, 2001; and Serial No. 60/338,172, filed Dec. 5, 2001. The disclosures of the aforementioned applications are incorporated by reference in their entireties.

TECHNICAL FIELD

This invention relates generally to catalysis of enantioselective reactions, and more particularly relates to the use of chiral organic compounds as catalysts for a variety of reactions involving α,β-unsaturated aldehydes as reactants.

BACKGROUND

Ancillary (or "spectator") ligand-metal coordination complexes (e.g., organometallic complexes) and compositions are useful as catalysts, stoichiometric reagents and therapeutic agents. The ancillary ligand contains functional groups that bind to one or more metal centers and remain associated therewith, providing an opportunity to modify the steric, electronic and chemical properties of the active sites of the complex, i.e., the metal centers.

Unfortunately, many organometallic reagents are expensive and depending on their catalytic activity may not be commercially viable. Moreover, many organometallic complexes are useful only for very specific chemical reactions and do not have broad utility as catalysts for a variety of different types of reactions. This problem may be emphasized for the catalysis of reactions leading to chiral molecules, particularly the conversion of either chiral or a chiral molecules via enantioselective catalysis to provide a chiral product.

Over the last 30 years enantioselective catalysis has become one of the most important frontiers in exploratory organic synthetic research. In the pharmaceutical industry and other industries, the use of pure enantiomeric molecules is often important for safety and efficacy. Thus, in the production of pharmaceuticals, use of catalysts or reagents that preferentially produce one enantiomer of a molecule relative to another enantiomer is particularly advantageous. Unfortunately, the catalysts that produce such enantiomers are typically organometallic complexes that are specific for a particular reaction. In addition, there is no way to predict with any reasonable accuracy which enantiomer will result. Examples of organometallic catalysts used to prepare chiral materials include BINOL-based complexes (Mikami et al. (1994) *J. Am. Chem. Soc.* 116:2812; Kobayashi et al. (1994) *J. Am. Chem. Soc.* 116:4083; Mikami et al. (1989) *J. Am. Chem. Soc.* 111:1940; Mikami et al. (1994) *J. Am. Chem. Soc.* 116:4077; Keck et al. (1993) *J. Am. Chem. Soc.* 115:8467; Keck et al. (1995) *J. Am. Chem. Soc.* 117:2363), BINAP-based complexes (Miyashita et al. (1980) *J. Am. Chem. Soc.* 102:7932; Miyashita et al. (1984) *Tetrahedron* 40:1245; Takaya et al. (1986) *J. Org. Chem.* 51:629; Takaya et al. (1988) *Org. Synth.* 67:20; Cai et al. (1995) *Tetrahedron Lett.* 36:7991), DUPHOS complexes (Burk et al. (1990) *Organometallics* 9:2653; Burk et al. (1993) *J. Am. Chem. Soc* 115:10125; Burk et al. (1992) *J. Am. Chem. Soc.* 114:6266; Burk et al. (1995) *J. Am. Chem. Soc.* 117:9375); salen-based complexes (i.e., organometallic complexes containing the N,N-bis(3,5-di-t-butylsalicylidene)-1,2-cyclohexane-diamino ligand; see, e.g., Li et al. (1993) *J. Am. Chem. Soc* 115:5326, and Evans et al. (1993) *Tetrahedron Lett.* 34:7027), and bisoxazoline-containing compounds (Evans et al. (1993) *J. Am. Chem. Soc.* 115:6460; Evans et al. (1997) *J. Am. Chem. Soc.* 119:7893; Evans et al. (1996) *Tetrahedron Lett.* 37:7481; Corey et al. (1992) *Tetrahedron Lett.* 33:6807; Gothelf al. (1996) *J. Org. Chem.* 61:346).

Despite the observed need and relatively few, narrow solutions, relatively few asymmetric transformations have been reported which employ organic molecules as reaction catalysts. There is tremendous potential for academic, economic and environmental benefit should versatile, chiral organic catalysts be developed. Only a few researchers have disclosed organic catalysts useful for preparing chiral materials. See, e.g., *Asymmetric Catalysis in Organic Synthesis*, Noyori, R., Ed. (New York: Wiley, 1994) and *Asymmetric Synthesis*, Ojima, I., Ed. (New York: VCH, 1993), and references cited therein. Also see Yang et al. (1998) *J. Am. Chem. Soc.* 120(24):5943–5952, who disclose the use of a dioxirane to catalyze enantioselective epoxidation, Shi et al. (1995) *J. Chem. Research* (S):46–47 (*J. Chem. Research* (M): 0401–0411), who disclose preparation of chiral quaternary ammonium salts stated to be useful as chiral phase-transfer catalysts by reaction of (R)-(+)-2,2-bis(bromomethyl)-6,6-dinitrobiphenyl and (R)-(+)-2,2-bis(bromomethyl)-1,1-binaphthyl with cyclic amines such as pyrrolidine, piperidine and 4-hydroxypiperidine. International Patent Publication No. WO 92/02505 to Castelijns also discloses use of a secondary amine in a catalytic transformation, i.e., in conversion of an unsaturated imine to a pyridine product, by reaction with an aldehyde or ketone.

Recently, however, certain organic catalysts have been disclosed as generally useful in a variety of enantioselective transformations, by lowering the LUMO (lowest unoccupied molecular orbital) of a reactant to facilitate reaction thereof. The organic catalysts are acid addition salts of nonmetallic compounds containing a Group 15 or Group 16 heteroatom, e.g., chiral amines, exemplified by the imidazolidinone salt (5S)-5-benzyl-2,2,3-trimethylimidazolidin-4-one hydrochloride (I)

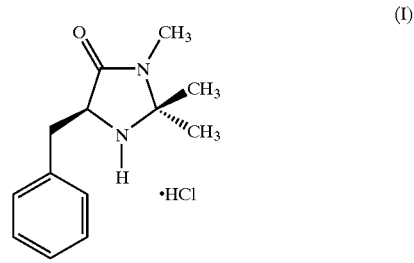

while exemplary reactants are α,β-unsaturated carbonyl compounds, including α,β-unsaturated aldehydes as well as α,β-unsaturated ketones. Such catalysts and reactions are described in U.S. Pat. No. 6,307,057 to MacMillan and U.S. Pat. No. 6,369,243 to MacMillan et al., which disclose the utility of (I) and other chiral amine salts in catalyzing a variety of reactions, including cycloaddition reactions, 1,4 nucleophile conjugate addition reactions, 1,4 radical addition reactions, organometallic insertion reactions, and ene reactions.

The use of catalyst (I) in the LUMO-lowering activation of α,β-unsaturated aldehydes, in particular, has been reported by Ahrendt et al. (2000) *J. Am. Chem. Soc.*

122:4243–4244, Jen et al. (2000) *J. Am. Chem. Soc.* 122:9874–9875, and Paras et al. (2001) *J. Am. Chem. Soc.* 123:4370–4371. The reaction proceeds via the reversible formation of an iminium ion intermediate, which can be in one of two enantiomeric configurations. Using propenal as a reactant and (I) as the catalyst, the possible iminium ion intermediates A and B are formed (Equation 1):

Equation 1:

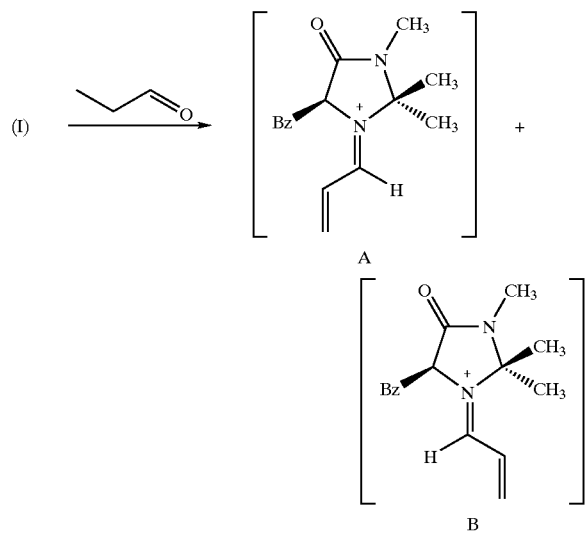

Upon further reaction, e.g., with cyclopentadiene in a Diels-Alder reaction, each intermediate results in a different enantiomeric product. That is, intermediate A gives rise to an exo product, while intermediate B results in the endo product (Equation 2):

Equation 2:

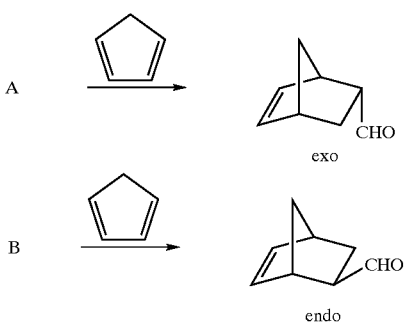

While imidazolidinone salt (I) and other chiral amines described in the foregoing references are quite valuable as enantioselective organic catalysts, there is a continuing need for nonmetallic catalysts that exhibit even higher levels of enantioselectivity across a diverse range of carbon-carbon bond forming reactions involving α,β-unsaturated carbonyl compounds as reactants. An ideal catalyst would be inexpensive and straightforward to synthesize, compatible with aerobic conditions, and provide for efficient reaction rates, good control over the geometry of the iminium ion intermediate, and high levels of enantiofacial discrimination. The invention is, in part, directed to such novel catalysts.

The invention is also directed to use of the novel catalysts in the alkylation of indoles and other bicyclic and polycyclic molecules containing at least one N-heterocyclic ring. With the commercial success of chiral pharmaceuticals has come an increasing demand for enantioselective methods to access structural motifs of established value in medicinal chemistry, and the indole structure has become widely identified as a "privileged pharmacophore" with implementation in over 40 medicinal agents of diverse therapeutic action. See Kleeman et al., *Pharmaceutical Substances* 4th Ed.; Kleeman, A.; Engel, J.; Kutscher, B.; Reichert, D. Thieme: Stuttgart, New York, 2001. Surprisingly, however, asymmetric entry to indolic architecture has been largely restricted to either the derivatization of enantiopure amino acids such as tryptophan (as in the synthesis of oxitriptan, or 5-hydroxytryptophan, the precursor to serotonin) or the optical resolution of racemic mixtures (as in the preparation of ramosetron, a 5-HT$_3$ antagonist; see Ohta et al. (1996) *Chem. Pharm. Bull.* 44:1707).

SUMMARY OF THE INVENTION

In one aspect of the invention, then, novel chiral catalysts are provided that address the aforementioned needs in the art, by enabling enantioselective reaction of α,β-unsaturated carbonyl compounds, particularly α,β-unsaturated aldehydes. The catalysts are nonmetallic, organic compounds, and thus avoid the problems associated with traditional organometallic catalysts. The present catalysts are readily synthesized from inexpensive, commercially available reagents, are compatible with aerobic conditions, and provide the desired products in excellent yields with a high level of enantioselectivity. The chiral catalysts are imidazolidinone compounds having the structure of formula (IIA) or (IIB)

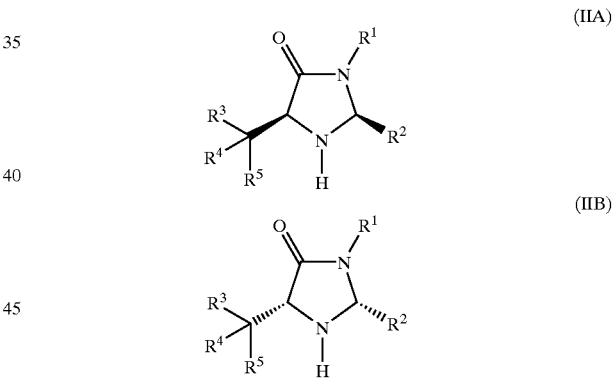

wherein:

$R^1$ is selected from the group consisting of $C_1$–$C_{12}$ hydrocarbyl, substituted $C_1$–$C_{12}$ hydrocarbyl, heteroatom-containing $C_1$–$C_{12}$ hydrocarbyl, and substituted heteroatom-containing $C_1$–$C_{12}$ hydrocarbyl;

$R^2$ has the structure —(L)$_m$—$CR^6R^7R^8$ wherein m is zero or 1, L is $C_1$–$C_6$ alkylene, and $R^6$, $R^7$ and $R^8$ are $C_1$–$C_{12}$ hydrocarbyl;

$R^3$ and $R^4$ are independently selected from the group consisting of hydrogen, halo, hydroxyl, $C_1$–$C_{12}$ hydrocarbyl, substituted $C_1$–$C_{12}$ hydrocarbyl, heteroatom-containing $C_1$–$C_{12}$ hydrocarbyl, and substituted heteroatom-containing $C_1$–$C_{12}$ hydrocarbyl; and $R^5$ is a cyclic group optionally substituted with 1 to 4 non-hydrogen substituents and containing zero to 3 heteroatoms, and also include acid addition salts thereof.

In another aspect of the invention, a process is provided for using imidazolidinone (IIA) or (IIB) to catalyze a reaction between an α,β-unsaturated aldehyde and a second reactant by lowering the energy level of the lowest unoccupied molecular orbital (LUMO) of the aldehyde. The process involves contacting an α,β-unsaturated aldehyde with the second reactant in the presence of (IIA) or (IIB), either in the form of an acid addition salt, or in the form of an electronically neutral compound combined with an acid.

The α,β-unsaturated aldehyde has the structure of formula (III)

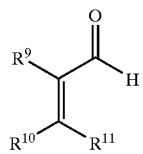

(III)

in which $R^9$, $R^{10}$ and $R^{11}$ are independently selected from the group consisting of hydrogen, $C_1$–$C_{30}$ hydrocarbyl, heteroatom-containing $C_1$–$C_{30}$ hydrocarbyl, substituted $C_1$–$C_{30}$ hydrocarbyl, substituted heteroatom-containing $C_1$–$C_{30}$ hydrocarbyl, and functional groups. The second reactant may be any compound that is capable of reacting with the α,β-unsaturated aldehyde by virtue of the lowered LUMO of the carbon-carbon double bond within the aldehyde in the presence of the imidazolidinone catalyst. The second reactant may or may not be covalently linked, directly or indirectly, to the first reactant, i.e., the reaction between the α,β-unsaturated aldehyde and the second reactant may be either intramolecular or intermolecular. Selection of the second reactant will depend on the reaction of interest; thus, for example, in a Diels-Alder reaction, the second reactant is a diene, while the first reactant, i.e., the α,β-unsaturated aldehyde, serves as a dienophile.

Examples of such reactions that may be catalyzed using the present compounds and methods include, without limitation, cycloaddition reactions, 1,4-nucleophile conjugate addition reactions, 1,4 radical addition reactions, organometallic insertion reactions (including Heck reactions), ene reactions, and any combination thereof (including reactions occurring in tandem or cascade).

Cycloaddition reactions include, for example, [2+2] cycloaddition, [3+2] cycloaddition and [4+2] cycloaddition, with the latter reactions exemplified by Diels-Alder reactions, inverse demand Diels-Alder reactions, and hetero Diels-Alder reactions. Other types of cycloaddition reactions that can be catalyzed using the compositions and methods of the invention are described, for example, by Gothelf et al. (1998) *Chem. Rev.* 98:863–909.

1,4 Nucleophile conjugate addition reactions, include 1,4 carbon addition (e.g., cyclopropanation), 1,4 amine addition (e.g., aziridination), 1,4 oxygen addition (e.g., epoxidation), 1,4 sulfur addition, 1,4 hydride addition, and 1,4 organometallic addition. Such reactions are examples of Michael additions, wherein the second reactant is a nucleophile containing a π bond, a lone pair bearing heteroatom, or a negative charge.

In a further aspect of the invention, the chiral catalysts of the invention are used in the alkylation of nitrogen-containing heterocycles, particularly bicyclic and polycyclic compounds containing at least one N-heterocyclic ring. Such reactants include, by way of example, compounds having the structure of formula (IV)

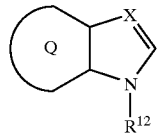

(IV)

wherein:
$R^{12}$ is selected from the group consisting of hydrogen, hydrocarbyl, substituted hydrocarbyl, heteroatom-containing hydrocarbyl, and substituted heteroatom-containing hydrocarbyl;

Q is a five- or six-membered aromatic ring containing zero to 3 heteroatoms selected from N, O and S and zero to 4 nonhydrogen substituents, wherein any two adjacent nonhydrogen substituents may together form an additional aryl, substituted aryl, heteroaryl, or heteroaryl substituent; and X is N or $CR^{13}$ wherein $R^{13}$ is hydrogen, hydrocarbyl, substituted hydrocarbyl, heteroatom-containing hydrocarbyl, or substituted heteroatom-containing hydrocarbyl.

In one preferred embodiment of the aforementioned reaction, compound (IV) is substituted at the 3-position with a moiety —$L^1$—Nu: (i.e., X is $CR^{13}$ where $R^{13}$ is —$L^1$—Nu:) wherein $L^1$ is a hydrocarbylene, substituted hydrocarbylene, heteroatom-containing hydrocarbylene, or substituted heteroatom-containing hydrocarbylene linker with 2 to 6 atoms in the linker backbone, and Nu: is a nucleophilic group capable of addition to an unsaturated bond, e.g., secondary amino, hydroxyl, or sulfhydryl, with secondary amino groups (including —NH-Prot wherein Prot is an amine protecting group such as butyloxycarbonyl, or "BOC") most preferred. The —$L^1$—Nu: substituent enables a subsequent reaction step in which Nu: adds to the double bond of the pyrrole ring. This cycloaddition step, following the initial reaction of compound (IV) with the α,β-unsaturated aldehyde, enables the straightforward synthesis of a variety of polycyclic compounds, including, by way of example, pyrroloindolines, a core structure having extensive utility in the development of a wide variety of therapeutic agents.

DETAILED DESCRIPTION OF THE DRAWINGS

Figure 1B:
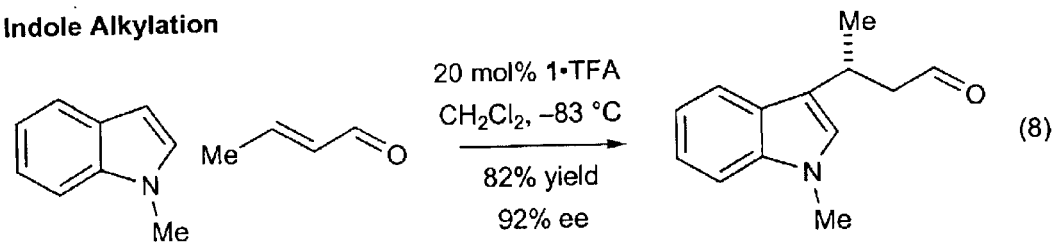
Figure 1B:
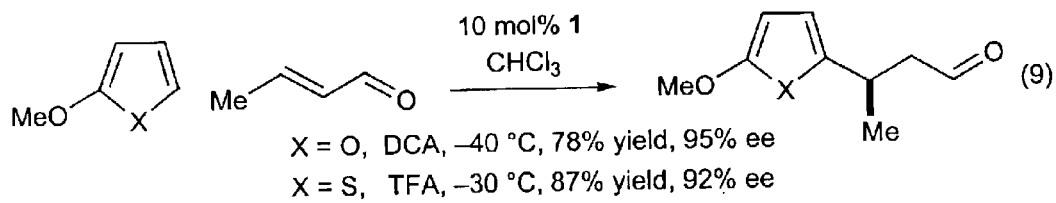
Figure 1B:
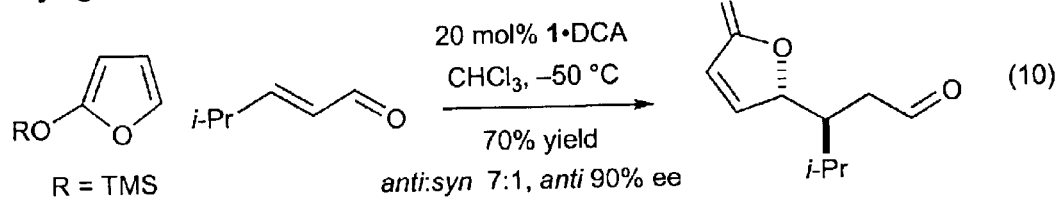
Figure 1B:
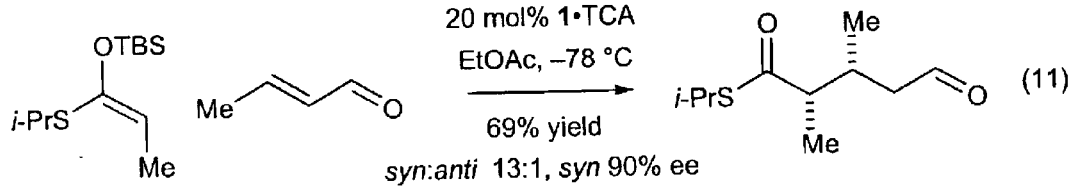
Figure 1B:
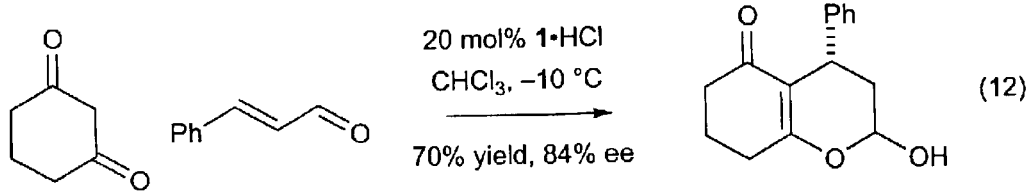

FIGS. 1A and 1B schematically illustrate the reactions of various α,β-unsaturated aldehydes catalyzed by acid addition salts of (2S,5S)-5-benzyl-2-tert-butyl-3-methylimidazolidin-4-one hydrochloride (1), as described in detail in Examples 2 through 12.

Figure 2:
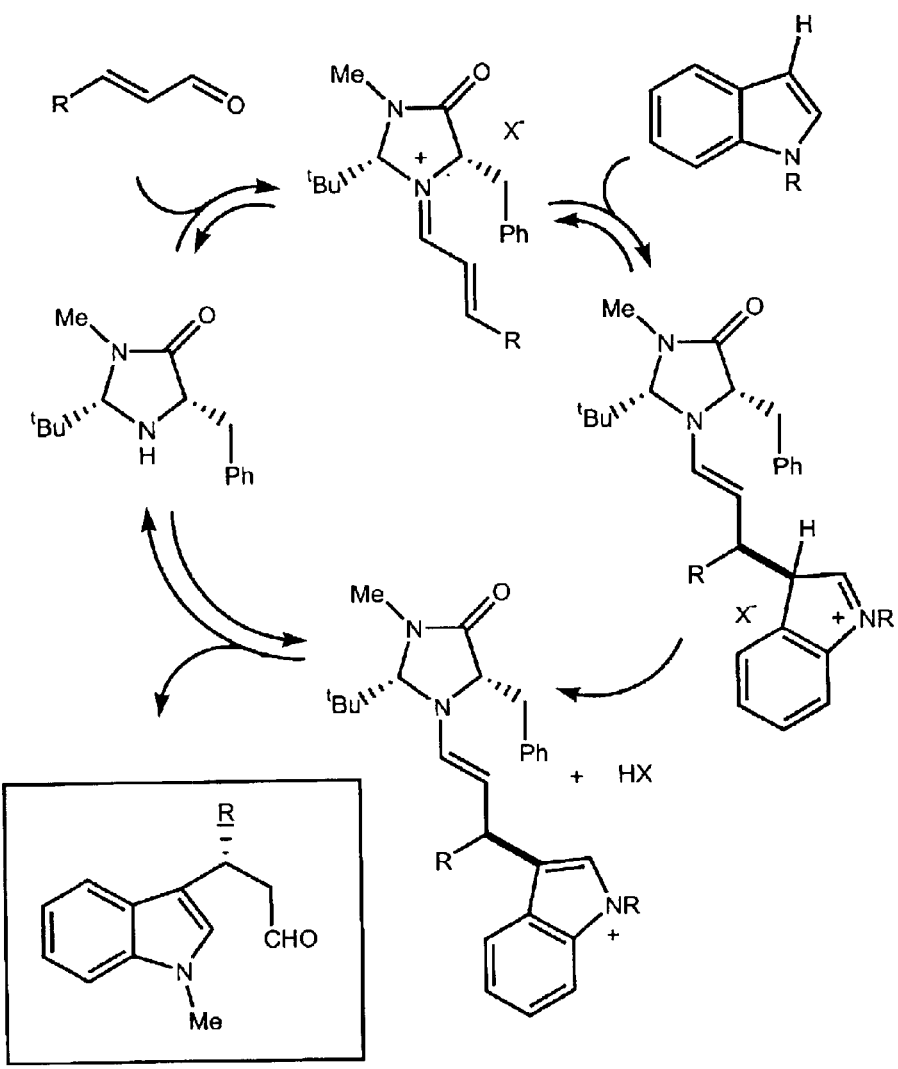

FIG. 2 schematically illustrates the catalytic cycle involved in organocatalytic indole alkylation using the catalysts and methods of the invention.

Figure 3:
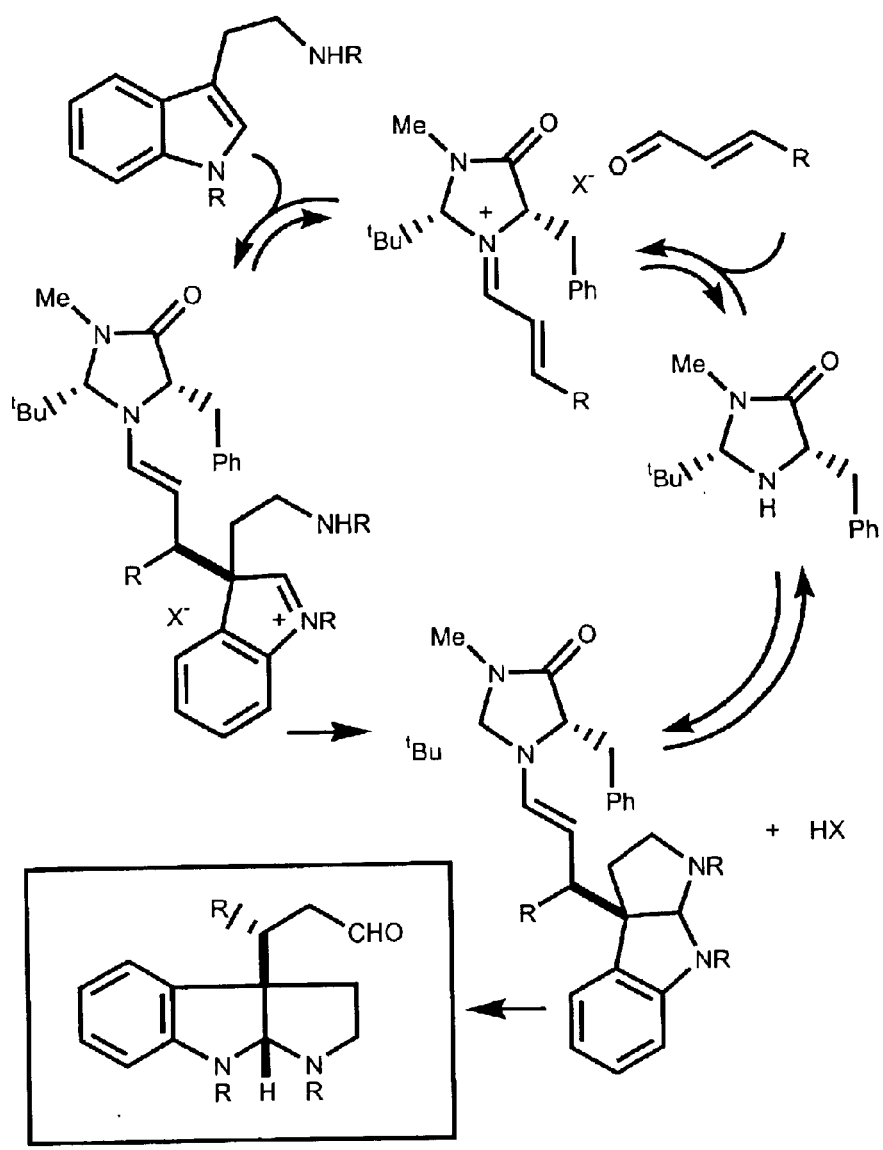

FIG. 3 schematically illustrates the catalytic cycle involved in organocatalytic pyrroloindoline alkylation using the catalysts and methods of the invention.

Figure 4:
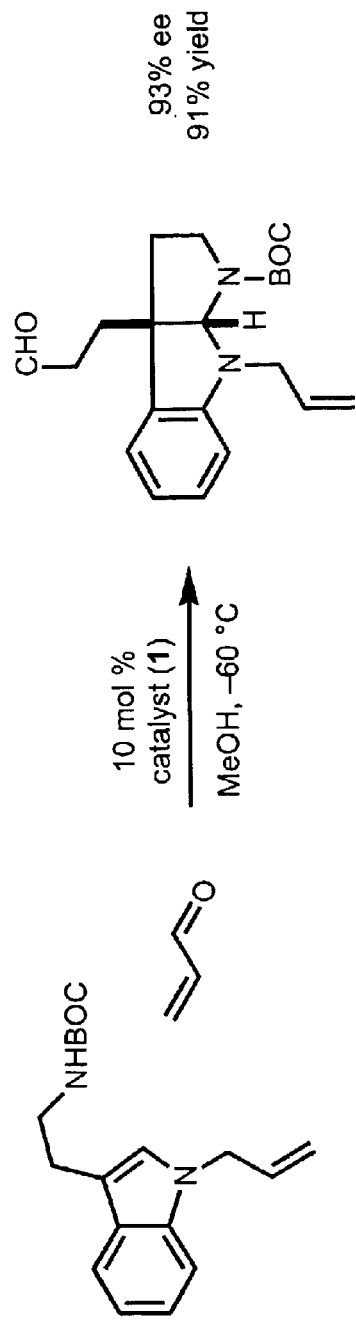
Figure 4:
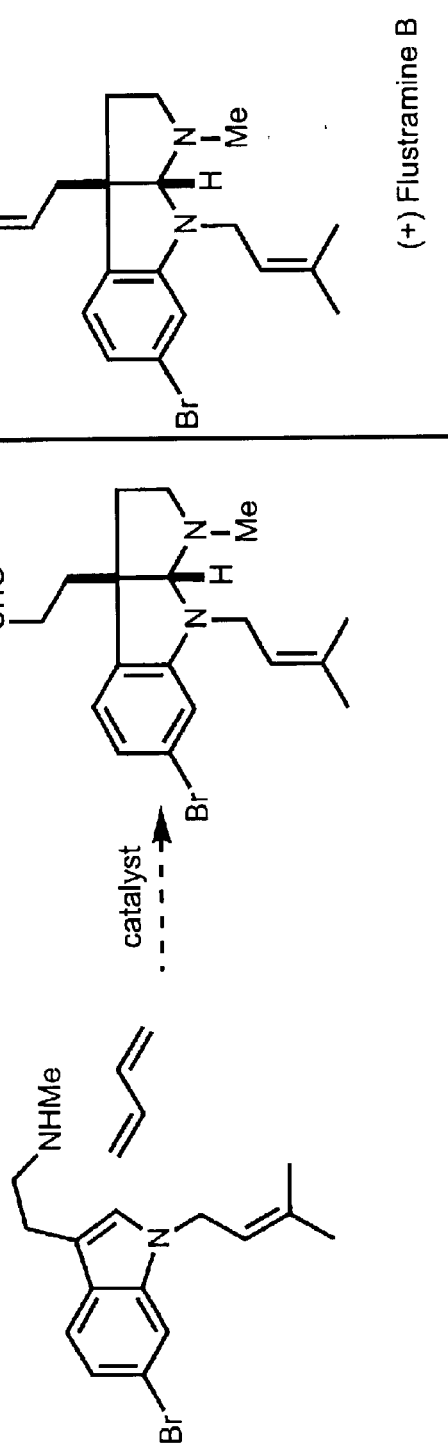

FIG. 4 schematically illustrates the synthesis of a pyrroloindoline "core" (3-(8-allyl-1-butyloxycarbonyl-2,3,8,8a-tetrahydro-1H-pyrrolo[2,3-b]indol-3a-yl)-propionaldehyde) from N-protected (i.e., butyloxycarbonyl-protected) 2-(1-allyl-1H-indol-3-yl)-ethylamine using the p-toluenesulfonic acid salt of (1), and indicates the utility of such a reaction in the synthesis of (+)-flustramine B.

Figure 5:
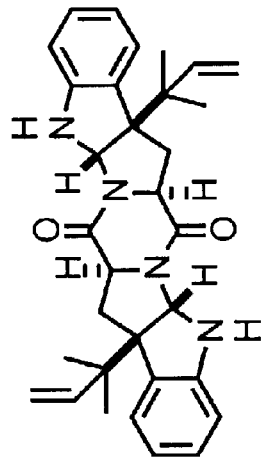
Figure 5:
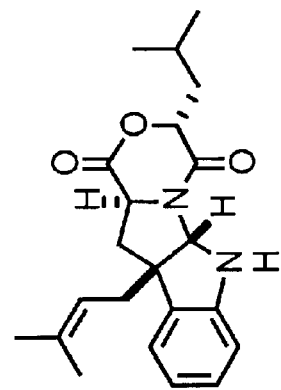
Figure 5:
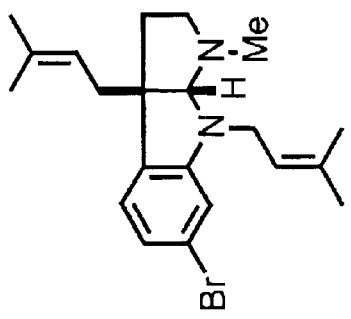
Figure 5:
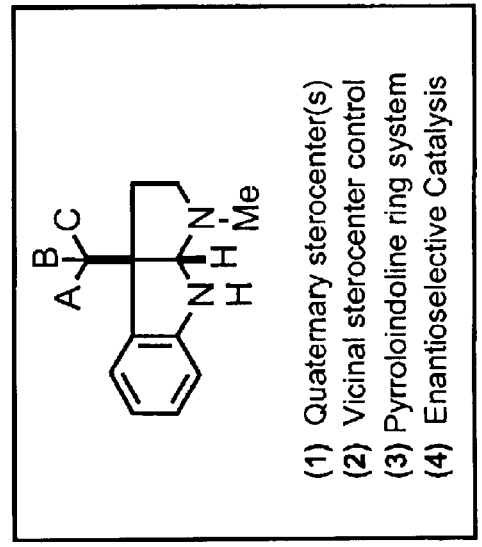
Figure 5:
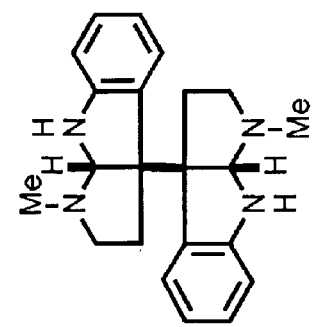
Figure 5:
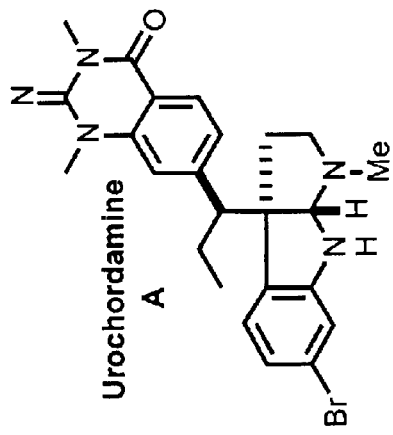

FIG. 5 sets forth the molecular structures of various natural products attainable using the catalysts and methods of the invention.

DETAILED DESCRIPTION OF THE PREFERRED EMBODIMENTS

I. Definitions and Nomenclature

Unless otherwise indicated, the invention is not limited to specific molecular structures, substituents, synthetic methods, reaction conditions, or the like, as such may vary. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise. Thus, for example, reference to "a catalyst" includes a single catalyst as well as a combination or mixture of two or more catalysts, reference to "a reactant" encompasses a combination or mixture of different reactants as well as a single reactant, and the like.

In this specification and in the claims that follow, reference will be made to a number of terms, which shall be defined to have the following meanings:

As used herein, the phrase "having the formula" or "having the structure" is not intended to be limiting and is used in the same way that the term "comprising" is commonly used. The term "independently selected from the group consisting of" is used herein to indicate that the recited elements, e.g., R groups or the like, can be identical or different.

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present.

The term "alkyl" as used herein refers to a branched or unbranched saturated hydrocarbon group typically although not necessarily containing 1 to about 24 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl and the like. Generally, although again not necessarily, alkyl groups herein contain 1 to about 18 carbon atoms, preferably 1 to about 12 carbon atoms. The term "lower alkyl" intends an alkyl group of 1 to 6 carbon atoms. "Substituted alkyl" refers to alkyl substituted with one or more substituent groups, and the terms "heteroatom-containing alkyl" and "heteroalkyl" refer to an alkyl substituent in which at least one carbon atom is replaced with a heteroatom, as described in further detail infra. If not otherwise indicated, the terms "alkyl" and "lower alkyl" include linear, branched, cyclic, unsubstituted, substituted, and/or heteroatom-containing alkyl or lower alkyl, respectively.

The term "alkenyl" as used herein refers to a linear, branched or cyclic hydrocarbon group of 2 to about 24 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, and the like. Generally, although again not necessarily, alkenyl groups herein contain 2 to about 18 carbon atoms, preferably 2 to 12 carbon atoms. The term "lower alkenyl" intends an alkenyl group of 2 to 6 carbon atoms. The term "substituted alkenyl" refers to alkenyl substituted with one or more substituent groups, and the terms "heteroatom-containing alkenyl" and "heteroalkenyl" refer to alkenyl in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl, respectively.

The term "alkynyl" as used herein refers to a linear or branched hydrocarbon group of 2 to 24 carbon atoms containing at least one triple bond, such as ethynyl, n-propynyl, and the like. Generally, although again not necessarily, alkynyl groups herein contain 2 to about 18 carbon atoms, preferably 2 to 12 carbon atoms. The term "lower alkynyl" intends an alkynyl group of 2 to 6 carbon atoms. The term "substituted alkynyl" refers to alkynyl substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include linear, branched, unsubstituted, substituted, and/or heteroatom-containing alkynyl and lower alkynyl, respectively.

The term "alkoxy" as used herein intends an alkyl group bound through a single, terminal ether linkage; that is, an "alkoxy" group may be represented as —O-alkyl where alkyl is as defined above. A "lower alkoxy" group intends an alkoxy group containing 1 to 6 carbon atoms, and includes, for example, methoxy, ethoxy, n-propoxy, isopropoxy, t-butyloxy, etc. Preferred substituents identified as "$C_1$–$C_6$ alkoxy" or "lower alkoxy" herein contain 1 to 3 carbon atoms, and particularly preferred such substituents contain 1 or 2 carbon atoms (i.e., methoxy and ethoxy).

The term "aryl" as used herein, and unless otherwise specified, refers to an aromatic substituent generally containing 5 to 30 carbon atoms and containing a single aromatic ring or multiple aromatic rings that are fused together, directly linked, or indirectly linked (such that the different aromatic rings are bound to a common group such as a methylene or ethylene moiety). Preferred aryl groups contain 5 to 20 carbon atoms, and particularly preferred aryl groups contain 5 to 12 carbon atoms. Exemplary aryl groups contain one aromatic ring or two fused or linked aromatic rings, e.g., phenyl, naphthyl, biphenyl, diphenylether, diphenylamine, benzophenone, and the like. "Substituted aryl" refers to an aryl moiety substituted with one or more substituent groups, and the terms "heteroatom-containing aryl" and "heteroaryl" refer to aryl substituent, in which at least one carbon atom is replaced with a heteroatom, as will be described in further detail infra. If not otherwise indicated, the term "aryl" includes unsubstituted, substituted, and/or heteroatom-containing aromatic substituents.

The term "aralkyl" refers to an alkyl group with an aryl substituent, and the term "alkaryl" refers to an aryl group with an alkyl substituent, wherein "alkyl" and "aryl" are as defined above. In general, aralkyl and alkaryl groups herein contain 6 to 30 carbon atoms, while preferred aralkyl and alkaryl groups contain 6 to 20 carbon atoms, and particularly preferred such groups contain 6 to 12 carbon atoms.

The term "amino" is used herein to refer to the group —$NZ^1Z^2$ wherein $Z^1$ and $Z^2$ are hydrogen or nonhydrogen substituents, with nonhydrogen substituents including, for example, alkyl, aryl, alkenyl, aralkyl, and substituted and/or heteroatom-containing variants thereof.

The terms "halo" and "halogen" are used in the conventional sense to refer to a chloro, bromo, fluoro or iodo substituent.

The term "heteroatom-containing" as in a "heteroatom-containing alkyl group" (also termed a "heteroalkyl" group) or a "heteroatom-containing aryl group" (also termed a "heteroaryl" group) refers to a molecule, linkage or substituent in which one or more carbon atoms are replaced with an atom other than carbon, e.g., nitrogen, oxygen, sulfur, phosphorus or silicon, typically nitrogen, oxygen or sulfur. Similarly, the term "heteroalkyl" refers to an alkyl substituent that is heteroatom-containing, the term "heterocyclic" refers to a cyclic substituent that is heteroatom-containing, the terms "heteroaryl" and heteroaromatic" respectively refer to "aryl" and "aromatic" substituents that are heteroatom-containing, and the like. Examples of heteroalkyl groups include alkoxyaryl, alkylsulfanyl-substituted alkyl, N-alkylated amino alkyl, and the like. Examples of heteroaryl substituents include pyrrolyl, pyrrolidinyl, pyridinyl, quinolinyl, indolyl, pyrimidinyl, imidazolyl, 1,2,4-triazolyl, tetrazolyl, etc., and examples of heteroatom-containing alicyclic groups are pyrrolidino, morpholino, piperazino, piperidino, etc.

"Hydrocarbyl" refers to univalent hydrocarbyl radicals containing 1 to about 30 carbon atoms, preferably 1 to about 24 carbon atoms, more preferably 1 to about 18 carbon atoms, most preferably about 1 to 12 carbon atoms, including linear, branched, cyclic, saturated and unsaturated species, such as alkyl groups, alkenyl groups, aryl groups, and the like. "Substituted hydrocarbyl" refers to hydrocarbyl substituted with one or more substituent groups, and the term "heteroatom-containing hydrocarbyl" refers to hydrocarbyl in which at least one carbon atom is replaced with a heteroatom. Unless otherwise indicated, the term "hydrocarbyl" is to be interpreted as including substituted and/or heteroatom-containing hydrocarbyl moieties.

By "substituted" as in "substituted hydrocarbyl," "substituted alkyl," "substituted aryl," and the like, as alluded to in some of the aforementioned definitions, is meant that in the hydrocarbyl, alkyl, aryl, or other moiety, at least one hydrogen atom bound to a carbon (or other) atom is replaced with one or more non-hydrogen substituents. Examples of such substituents include, without limitation: functional groups such as halo, hydroxyl, sulfhydryl, $C_1$–$C_{24}$ alkoxy, $C_2$–$C_{24}$ alkenyloxy, $C_2$–$C_{24}$ alkynyloxy, $C_5$–$C_{20}$ aryloxy, acyl (including $C_2$–$C_{24}$ alkylcarbonyl (—CO-alkyl) and $C_6$–$C_{20}$ arylcarbonyl (—CO-aryl)), acyloxy (—O-acyl), $C_2$–$C_{24}$ alkoxycarbonyl (—(CO)—O-alkyl), $C_6$–$C_{20}$ aryloxycarbonyl (—(CO)—O-aryl), halocarbonyl (—CO)—X where X is halo), $C_2$–$C_{24}$ alkylcarbonato (—O—(CO)—O-alkyl), $C_6$–$C_{20}$ arylcarbonato (—O—(CO)—O-aryl), carboxy (—COOH), carboxylato (—COO$^-$), carbamoyl (—(CO)—NH$_2$), mono-substituted $C_1$–$C_{24}$ alkylcarbamoyl (—(CO)—NH($C_1$–$C_{24}$ alkyl)), di-substituted alkylcarbamoyl (—(CO)—N($C_1$–$C_{24}$ alkyl)$_2$), mono-substituted arylcarbamoyl (—(CO)—NH-aryl), thiocarbamoyl (—(CS)—NH$_2$), carbamido (—NH—(CO)—NH$_2$), cyano (—C≡N), isocyano (—N$^+$≡C$^-$), cyanato (—O—C≡N), isocyanato (—O—N$^+$≡C$^-$), isothiocyanato (—S—C≡N), azido (—N=N$^+$=N$^-$), formyl (—(CO)—H), thioformyl (—(CS)—H), amino (—NH$_2$), mono- and di-($C_1$–$C_{24}$ alkyl)-substituted amino, mono- and di-($C_5$–$C_{20}$ aryl)-substituted amino, $C_2$–$C_{24}$ alkylamido (—NH—(CO)-alkyl), $C_5$–$C_{20}$ arylamido (—NH—(CO)-aryl), imino (—CR=NH where R=hydrogen, $C_1$–$C_{24}$ alkyl, $C_5$–$C_{20}$ aryl, $C_6$–$C_{20}$ alkaryl, $C_6$–$C_{20}$ aralkyl, etc.), alkylimino (—CR=N(alkyl), where R=hydrogen, alkyl, aryl, alkaryl, etc.), arylimino (—CR=N(aryl), where R=hydrogen, alkyl, aryl, alkaryl, etc.), nitro (—NO$_2$), nitroso (—NO), sulfo (—SO$_2$—OH), sulfonato (—SO$_2$—O—), $C_1$–$C_{24}$ alkylsulfanyl (—S-alkyl; also termed "alkylthio"), arylsulfanyl (—S-aryl; also termed "arylthio"), $C_1$–$C_{24}$ alkylsulfinyl (—(SO)-alkyl), $C_5$–$C_{20}$ arylsulfinyl (—(SO)-aryl), $C_1$–$C_{24}$ alkylsulfonyl (—SO$_2$-alkyl), $C_5$–$C_{20}$ arylsulfonyl (—SO$_2$-aryl), phosphono (—P(O)(OH)$_2$), phosphonato (—P(O)(O$^-$)$_2$), phosphinato (—P(O)(O$^-$)), phospho (—PO$_2$), and phosphino (—PH$_2$); and the hydrocarbyl moieties $C_1$–$C_{24}$ alkyl (preferably $C_1$–$C_{18}$ alkyl, more preferably $C_1$–$C_{12}$ alkyl, most preferably $C_1$–$C_6$ alkyl), $C_2$–$C_{24}$ alkenyl (preferably $C_2$–$C_{18}$ alkenyl, more preferably $C_2$–$C_{12}$ alkenyl, most preferably $C_2$–$C_6$ alkenyl), $C_2$–$C_{24}$ alkynyl (preferably $C_2$–$C_{18}$ alkynyl, more preferably $C_2$–$C_{12}$ alkynyl, most preferably $C_2$–$C_6$ alkynyl), $C_5$–$C_{30}$ aryl (preferably $C_5$–$C_{20}$ aryl, more preferably $C_5$–$C_{12}$ aryl), and $C_6$–$C_{30}$ aralkyl (preferably $C_6$–$C_{20}$ aralkyl, more preferably $C_6$–$C_{12}$ aralkyl). In addition, the aforementioned functional groups may, if a particular group permits, be further substituted with one or more additional functional groups or with one or more hydrocarbyl moieties such as those specifically enumerated above. Analogously, the above-mentioned hydrocarbyl moieties may be further substituted with one or more functional groups or additional hydrocarbyl moieties such as those specifically enumerated.

When the term "substituted" appears prior to a list of possible substituted groups, it is intended that the term apply to every member of that group. For example, the phrase "substituted alkyl and aryl" is to be interpreted as "substituted alkyl and aryl."

The terms "LUMO" and "HOMO" (abbreviations for lowest unoccupied molecular orbital and highest occupied molecular orbital, respectively) refer to the frontier orbitals of two reactants (such as a diene and dienophile, in a Diels-Alder reaction), with the LUMO referring to the vacant orbital of lowest energy, in a first reactant (i.e., in an α,β-unsaturated aldehyde as described herein), and the HOMO referring to the orbital containing electrons of highest energy, in a second reactant.

The term "chiral" refers to a structure that does not have an improper rotation axis ($S_n$), i.e., it belongs to point group $C_n$ or $D_n$. Such molecules are thus chiral with respect to an axis, plane or center of asymmetry. Preferred "chiral" molecules herein are in enantiomerically pure form, such that a particular chiral molecule represents at least about 95 wt. % of the composition in which it is contained, more preferably at least about 99 wt. % of that composition.

The term "enantioselective" refers to a chemical reaction that preferentially results in one enantiomer relative to a second enantiomer, i.e., gives rise to a product of which a desired enantiomer represents at least about 50 wt. %. Preferably, in the enantioselective reactions herein, the desired enantiomer represents at least about 85 wt. % of the product, optimally at least about 95 wt. % of the product.

In the molecular structures herein, the use of bold and dashed lines to denote particular conformation of groups follows the IUPAC convention. A bond indicated by a broken line indicates that the group in question is below the general plane of the molecule as drawn (the "α" configuration), and a bond indicated by a bold line indicates that the group at the position in question is above the general plane of the molecule as drawn (the "β" configuration).

II. The Novel Catalysis

In one embodiment, then, chiral imidazolidinone compounds are provided for catalyzing an enantioselective reaction of an α,β-unsaturated aldehyde by lowering the LUMO of the carbon-carbon double bond within the aldehyde. The reaction will generally involve a second reactant that is capable of undergoing reaction with the activated α,β-unsaturated aldehyde, but the invention additionally encompasses intramolecular reactions as well, wherein the second "reactant" is directly or indirectly bound to the aldehyde.

The chiral imidazolidinone compounds have the structure of formula (IIA) or (IIB)

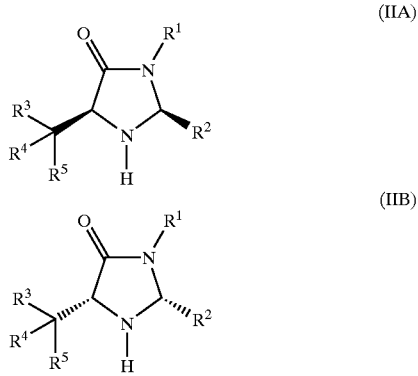

and may be in the form of an acid addition salt. In the reactions described herein, the catalyst used is either an acid addition salt of compound (IIA) or (IIB), or an acid is added to the reaction mixture to serve as a co-catalyst for compound (IIA) or (IIB) in electronically neutral form.

In formulae (IIA) and (IIB), the various substituents are as follows:

$R^1$ is selected from the group consisting of $C_1$–$C_{12}$ hydrocarbyl (e.g., alkyl, alkenyl, alkynyl, aryl, alkaryl, aralkyl, etc.), substituted $C_1$–$C_{12}$ hydrocarbyl (e.g., substituted alkyl, alkenyl, alkynyl, aryl, alkaryl, aralkyl, etc.), heteroatom-containing $C_1$–$C_{12}$ hydrocarbyl (e.g., heteroatom-containing alkyl, alkenyl, alkynyl, aryl, alkaryl, aralkyl, etc.), and substituted heteroatom-containing $C_1$–$C_{12}$ hydrocarbyl (e.g., substituted heteroatom-containing alkyl, alkenyl, alkynyl, aryl, alkaryl, aralkyl, etc.). Preferred $R^1$ substituents are $C_1$–$C_{12}$ hydrocarbyl such as $C_1$–$C_{12}$ alkyl, with $C_1$–$C_6$ alkyl groups (e.g., methyl) particularly preferred.

$R^2$ has the structure —(L)$_m$—CR$^6$R$^7$R$^8$ wherein m is zero or 1, L is $C_1$–$C_6$ alkylene, and $R^6$, $R^7$ and $R^8$ are $C_1$–$C_{12}$ hydrocarbyl. This is in contrast to prior imidazolidinone catalysts such as those described in Ahrendt et al. (2000) *J. Am. Chem. Soc.* 122:4243–4244, and Jen et al. (2000) *J. Am. Chem. Soc.* 122:9874–9875, in which the imidazolidinone is di-substituted at the 2-position with methyl groups. Here, the 2-position is substituted with a single group, $R^2$, relieving the steric obstruction immediately adjacent to the heterocycle in the catalysts of Ahrendt et al. and Jen et al. In a preferred embodiment, m is zero, $R^6$, $R^7$ and $R^8$ are $C_1$–$C_{12}$ alkyl. Optimally, $R^6$, $R^7$ and $R^8$ are $C_1$–$C_6$ alkyl, e.g., methyl (such that $R^2$ is then a tert-butyl group).

$R^3$ and $R^4$ are independently selected from the group consisting of hydrogen, halo, hydroxyl, $C_1$–$C_{12}$ hydrocarbyl, substituted $C_1$–$C_{12}$ hydrocarbyl, heteroatom-containing $C_1$–$C_{12}$ hydrocarbyl, and substituted heteroatom-containing $C_1$–$C_{12}$ hydrocarbyl. Preferably, $R^3$ and $R^4$ are hydrogen or $C_1$–$C_{12}$ hydrocarbyl, and, optimally, $R^3$ and $R^4$ are both hydrogen.

$R^5$ is a cyclic group optionally substituted with 1 to 4 non-hydrogen substituents and containing zero to 3 heteroatoms generally selected from N, O, and S. In a preferred embodiment, $R^5$ is monocyclic aryl or heteroaryl optionally substituted with 1 to 4 substituents selected from the group consisting of halo, hydroxyl, and $C_1$–$C_{12}$ hydrocarbyl. More preferably, $R^5$ is phenyl optionally substituted with 1 or 2 substituents selected from the group consisting of halo, hydroxyl, and $C_1$–$C_6$ alkyl, and in a particularly preferred embodiment, $R^5$ is an unsubstituted phenyl group.

The acid used to form the imidazolidinone salt or employed as a co-catalyst for the electronically neutral compound is generally a Bronsted acid. Suitable Bronsted acids are generally although not necessarily generally although not necessarily selected from acids having a pKa of less than about 5.

Combinations of Bronsted acids may also be used. Suitable acids include both organic and inorganic acids, with inorganic acids including, but not limited to, hydrochloric acid, hydrobromic acid, sulfuric acid, sulfurous acid, nitric acid, nitrous acid, perchloric acid, phosphoric acid, and chromic acid, and with organic acids exemplified by carboxylic acids, sulfonic acids, phosphonic acids, and aromatic alcohols, e.g., phenols, substituted with 1 to 5 electron-withdrawing substituents such as nitro, cyano, sulfonato, halo (i.e., Cl, F, Br or I) and halogenated alkyl (typically fluorinated alkyl, preferably perfluorinated lower alkyl such as trifluoromethyl). Particularly suitable organic acids are carboxylic acids and sulfonic acids having the structural formulas $R^x$—COOH and $R^x$—SO$_2$—OH wherein $R^x$ is aryl, alkyl, substituted aryl (e.g., halogenated aryl), or substituted alkyl (e.g., halogenated alkyl, particularly fluorinated and chlorinated alkyl). Preferred $R^x$ groups are methyl, halogenated methyl (e.g., fluorinated methyl such as trifluoromethyl, chlorinated methyl such as chloromethyl, dichloromethyl, and trichloromethyl, etc.), and nitrite-substituted methyl. Specific examples of preferred organic acids include acetic acid, propionic acid, glycolic acid, pyruvic acid, oxalic acid, malic acid, malonic acid, succinic acid, maleic acid, fumaric acid, tartaric acid, citric acid, benzoic acid, 2-nitrobenzoic acid, cinnamic acid, mandelic acid, methanesulfonic acid, ethanesulfonic acid, triflic acid, p-toluene sulfonic acid, salicylic acid, chloroacetic acid, dichloroacetic acid, trichloroacetic acid, trifluoroacetic acid, and combinations thereof. The Bronsted acid may or may not be chiral, and those Bronsted acids that are chiral may be used in isomerically pure form or as a racemic mixture.

Acid addition salts of the imidazolidinone may be synthesized by admixing the imidazolidinone (in uncharged, free base form) with a Bronsted acid HX, at a desired molar ratio, generally in the range of approximately 1:100 to 100:1, typically about 1:10 to 10:1, preferably about 1:2 to 2:1. Alternatively, the uncharged imidazolidinone may be combined with at least one salt $M^{q+}q(X^-)$, thereby forming the desired imidazolidinone salt via ion exchange. A wide variety of salts may be used for this latter purpose, and the cation $M^{+q}$ can be virtually any cation, although q is generally 1, 2 or 3. Suitable M elements are typically chosen from Groups 2 to 13 of the Periodic Table of the Elements, but M may also be a polyatomic cation such as the ammonium ion $NH_4^+$. It should also be noted that the imidazolidinone salt can be prepared with two or more different Bronsted acids or metal salts, thereby forming a mixture of imidazolidinone salts, i.e., salts containing different anions $X^-$.

For purposes of exemplification, a detailed description of one method for synthesizing the imidazolidinone salt (2S, 5S)-5-benzyl-2-tert-butyl-3-methylimidazolidin-4-one hydrochloride ((5S)-5-benzyl-2,2,3-trimethylimidazolidin-4-one hydrochloride) is described in Example 1.

III. Reactions

In another embodiment, a process is provided for using imidazolidinone (IIA) or (IIB) to catalyze a reaction between an α,β-unsaturated aldehyde and a second reactant by lowering the energy level of the lowest unoccupied molecular orbital (LUMO) of the aldehyde. The process involves contacting an α,β-unsaturated aldehyde with the second reactant in the presence of a catalyst composed of imidazolidinone (IIA) or (IIB), either in the form of an acid addition salt as described in the preceding section, or in the form of an electronically neutral compound combined with a Bronsted acid. The second reactant is one that is capable of reacting with the aldehyde by virtue of the lowered LUMO of the aldehyde in the presence of the catalyst.

The α,β-unsaturated aldehyde has the structure of formula (III)

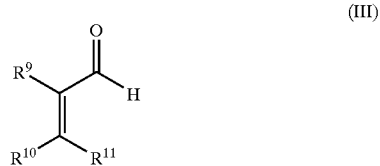

in which $R^9$, $R^{10}$ and $R^{11}$ are independently selected from the group consisting of hydrogen, $C_1$–$C_{30}$ hydrocarbyl, heteroatom-containing $C_1$–$C_{30}$ hydrocarbyl, substituted $C_1$–$C_{30}$ hydrocarbyl, substituted heteroatom-containing $C_1$–$C_{30}$ hydrocarbyl, and functional groups. In a preferred embodiment, $R^9$, $R^{10}$ and $R^{11}$ are independently selected from the group consisting of hydrogen, $C_1$–$C_{24}$ alkyl, $C_2$–$C_{24}$ alkenyl, $C_2$–$C_{24}$ alkynyl, $C_1$–$C_{24}$ alkoxy, $C_2$–$C_{24}$ alkenyloxy, $C_2$–$C_{24}$ alkynyloxy, $C_5$–$C_{30}$ aryl, $C_5$–$C_{30}$ aryloxy, $C_2$–$C_{24}$ alkoxyalkyl, $C_6$–$C_{30}$ aryloxyalkyl, hydroxyl, sulfhydryl, $C_2$–$C_{24}$ alkylcarbonyl, $C_6$–$C_{30}$ arylcarbonyl, $C_2$–$C_{24}$ alkoxycarbonyl, $C_6$–$C_{30}$ aryloxycarbonyl, halocarbonyl, $C_2$–$C_{24}$ alkylcarbonato, $C_6$–$C_{30}$ arylcarbonato, carboxy, carboxylato, carbamoyl, mono- and di-($C_1$–$C_{24}$ alkyl)-substituted carbamoyl, mono- and di-($C_5$–$C_{20}$ aryl)-substituted carbamoyl, amino, mono- and di-($C_1$–$C_{24}$ alkyl)-substituted amino, mono- and di-($C_5$–$C_{20}$ aryl)-substituted amino, $C_2$–$C_{24}$ alkylamido, $C_6$–$C_{30}$ arylamido, imino, $C_2$–$C_{24}$ alkylimino, $C_6$–$C_{30}$ arylimino, nitro, nitroso, sulfo, sulfonato, $C_1$–$C_{24}$ alkylsulfanyl, $C_5$–$C_{30}$ arylsulfanyl, $C_1$–$C_{24}$ alkylsulfinyl, $C_5$–$C_{30}$ arylsulfinyl, $C_1$–$C_{24}$ alkylsulfonyl, $C_5$–$C_{30}$ arylsulfonyl, phosphono, phosphonato, phosphinato, phospho, phosphino, and combinations thereof. In addition, any two of $R^9$, $R^{10}$ and $R^{11}$ taken together can form a cyclic structure selected from five-membered rings, six-membered rings, and fused five-membered and/or six-membered rings, wherein the cyclic structure is aromatic, alicyclic, heteroaromatic, or heteroalicyclic, and has zero to 4 non-hydrogen substituents and zero to 3 heteroatoms.

In an exemplary embodiment, $R^9$ and $R^{11}$ are hydrogen, and $R^{10}$ is selected from hydrogen, $C_1$–$C_{12}$ alkyl, $C_1$–$C_{12}$ alkoxy, $C_5$–$C_{20}$ aryl, $C_2$–$C_{12}$ alkoxyalkyl, and $C_6$–$C_{20}$ aryloxyalkyl. Preferably, $R^{10}$ is hydrogen, $C_1$–$C_6$ alkyl, $C_5$–$C_{12}$ aryl, or $C_6$–$C_{12}$ aryloxyalkyl.

The second reactant may be any compound that is capable of reacting with the α,β-unsaturated aldehyde by virtue of the lowered LUMO of the carbon-carbon double bond within the aldehyde in the presence of the imidazolidinone catalyst. The second reactant may or may not be covalently linked, directly or indirectly, to the first reactant, i.e., the reaction between the first and second reactants may be either intramolecular or intermolecular. Selection of the second reactant will depend on the reaction of interest; thus, for example, in a Diels-Alder reaction, the second reactant is a diene, while the first reactant, i.e., the α,β-unsaturated aldehyde, serves as a dienophile. Examples of various reactants and corresponding reaction types are discussed in further detail below.

An acid addition salt of the imidazolidinone salt may also be combined with excess imidazolidinone in electronically neutral form to tune the reaction, i.e., improving catalytic activity, conversion or selectivity. The molar ratio of the imidazolidinone to the anionic counterion of the acid can be as high as about 100:1, although typically not exceeding about 20:1, and most typically not exceeding about 2:1.

As demonstrated in equations 3–12 of FIGS. 1A and 1B, the imidazolidinones of the invention are highly effective asymmetric catalysts for a broad range of new and traditional carbon-carbon bond forming reactions. Examples 2 and 3, for example, corresponding to equations 3 and 4 of FIG. 1A, document that (2S,5S)-5-benzyl-2-tert-butyl-3-methylimidazolidin-4-one hydrochloride (1) (prepared as described in Example 1), a representative catalyst of the invention, allow enantioselective access (93% ee) to complex six-membered ring systems arising from either inter- or intramolecular Diels-Alder cycloaddition. Notably, the bimolecular [4+2] reaction (Example 2, equation 3) is accomplished with exo diastereoselectivity to provide a bridged bicyclic isomer that is traditionally not available using metal mediated or thermally activated Diels-Alder conditions. See: (a) Bao et al. (1993) *J. Am. Chem. Soc.* 115:3814–3815; (b) Corey et al. (1991) *J. Am. Chem. Soc.* 113 :8966–8967; (c) Corey et al. (1993) *Tetrahedron Lett.* 34:3979–3982; (d) Furuta et al. (1989) *J. Org. Chem.* 54:1481–1483; (e) Hashimoto et al. (1979) *J. Chem. Soc., Chem. Commun.*, 437–438; (f) Ishihara et al. (1993) *J. Org. Chem.* 58:6917–6919;(g) Ishihara et al. (1994) *J. Am. Chem. Soc.* 116 :1561–1562; (h) Jones et al. (2000) *Tetrahedron: Asymmetry* 11: 4303–4320; (i) Kundig et al.(1999) *Angew. Chem.-Int. Edit. Engl.* 38:1220–1223.

With respect to the intramolecular Diels-Alder (IMDA) reaction, it is important to note that the present catalyst and methodology provides only the second example of an enantioselective IMDA that employs α,β-unsaturated aldehydes (see Ishikara et al. (1996) *J. Am. Chem. Soc.* 118:3049–3050). The majority of chiral Lewis acid catalyzed IMDA reactions carried out previously have been achieved using dienophile tethers that incorporate chelating auxiliaries. Evans et al. (1997) *J. Org. Chem.* 62:786–787; Iwasawa et al. (1989) *Chem. Lett*, 1947–1950.

The imidazolidinones of the invention are also useful in the catalysis of [3+2] nitrone cycloadditions to provide enantioenriched isoxazolidines (Example 4, equation 5 of FIG. 1A; 98% ee), valuable synthons for the construction of biologically important amino acids, β-lactams, amino carbohydrates and alkaloids. See Frederickson (1997) *Tetrahedron* 53:403, which provides a review of the utility of amino-oxy synthons.

In comparison to nitrone cycloaddition reactions catalyzed with 2-dimethyl analogs of the present imidazolidinone compounds—i.e., (5S)-5-benzyl-2,2,3-trimethylimidazolidin-4-one hydrochloride, described by Jen et al. (2000) *J. Am. Chem. Soc.* 122:9874–987—the catalysts of the present invention exhibit superior reaction rates, yield, diastereoselectivities and enantiocontrol. That is, with a representative catalyst of the invention, a nitrone cycloaddition reaction proceeds to completion in under 11 hours with a 96% yield, an endo:exo ratio of 150:1 and 98% ee in the endo product (see Example 4). By contrast, Jen et al. (2000) obtained yields of 45% to a maximum of 77%, an enantiomeric (exo:endo) ratio in the range of 33:66 to 88:12, and an average of 63% ee in the endo product.

Other types of cycloaddition reactions that can be catalyzed using the compositions and methods of the invention are described, for example, by Gothelf et al. (1998) *Chem. Rev.* 98:863–909.

The catalysts of the invention also exhibit utility as enantioselective Friedel-Crafts alkylation catalysts. As illustrated in Equations 6–9 of FIGS. 1A and 1B, and as documented in Examples 5–8, the conjugate addition of a diverse range of aromatic nucleophiles (anilines, pyrroles, indoles, furans and thiophenes) can be achieved in a synthetically straightforward manner with excellent levels of enantioselectivity (90–95% ee). It should be noted that for each aromatic class represented, the depicted reaction exemplifies the first enantioselective Friedel-Crafts alkylation (organo- or metal catalyzed) involving α,β-unsaturated aldehydes. Previously, the only enantioselective reactions involving additions of indoles, furans and catechols to α,β-unsaturated keto-esters and imines were catalyzed by metallic catalysts. See Jensen et al. (2001) *Angew. Chem.-Int. Edit. Engl.* 40:160; and Johannsen (1999) *Chem. Commun.* 2233.

Significantly, the novel imidazolidinones of the invention can facilitate the conjugate addition of electron-rich benzene systems to generate enantioenriched benzylic stereogenicity, an important chiral synthon for the preparation of natural products (a 2001 survey of the Beilstein database documents over 5000 naturally occurring structures that exhibit benzylic stereogenicity) as well as synthetic medicinal agents. The latter include, by way of example, sertraline (Zoloft®), tolteridine (Detrol®), and paroxetine (Paxil®), relevant syntheses of which are described by McRae et al. (2001) *Expert Opin. Pharm.* 2:883–892, Hills et al. (1998) *Drugs* 55:813–820, and Heydorn (1999) *Expert Opin. Invest. Drugs* 8:417–441, respectively. A representative Friedel-Crafts alkylation reaction, illustrated by Equation 6 of FIG. 1A, involves the addition of 1-phenylpyrrolidine to methyl 4-oxobutenoate, and is described in detail in Example 5. The reaction is accomplished at room temperature in 20 minutes (10 mol % catalyst, 96% yield) to provide the disubstituted benzene adduct in 95% ee. This organocatalytic Friedel-Crafts protocol also provides rapid access to 3-substituted chiral indoles (Equation 8 of FIG. 1B; Example 7), a structural motif that is not readily accessible in enantiopure form using conventional catalytic methods, but is nevertheless commonly found in medicinal chemistry, for example, in: COX-2 inhibitors (Black et al. (1996) *Bioorg. Med. Chem. Lett.* 6:25); N-methyl-D-aspartate (NMDA)-glycine antagonists (Katayama et al. (2001) *J. Org. Chem.* 66:3473); antileukemia agents (Boido-Canu et al. (1988) *Farmaco Ed. Sci.*, 43:801; Matsumoto et al. (1987) *Heterocycles* 26:1743–1746); and antibacterial agents (Witty et al. (1996) *Bioorg. Med Chem. Lett.*,6:1375; Matsuda et al. (1998) *J. Agric. Food Chem.* 46:4416; El-Ablak et al. (1995) *Boll. Chim. Farm.* 134:77).

The catalysts of the invention are also useful in facilitating a variety of 1,4 nucleophile conjugate addition reactions, including 1,4 carbon addition (e.g., cyclopropanation), 1,4 amine addition (e.g., aziridination), and 1,4 oxygen addition (e.g., epoxidation), 1,4 sulfur addition, 1,4 hydride addition, and 1,4 organometallic addition. Such reactions are examples of Michael additions, wherein an (α,β-unsaturated aldehyde undergoes reaction with a nucleophile containing π bond, a lone pair bearing heteroatom, or a negative charge.

More specifically, the capacity of the imidazolidinone catalysts of the invention to mediate the enantioselective addition of enolic nucleophiles to (α,β-unsaturated aldehydes has been demonstrated with various nucleophilic reactants, as illustrated in Equations 10–12 of FIG. 1B and as documented in Examples 9–11. For example, a range of silyloxy furans can be enantioselectively coupled with enals in a vinylogous Michael addition to provide 3-substituted butenolides with useful anti isomer selectivity; see Example 9 and Equation 10 (70% yield, anti:syn 7:1, 90% ee). As shown in Equation 11, and as demonstrated in Example 10, the addition of silylketene acetals to crotonaldehyde provides high levels of enantiocontrol in the formation of syn-2,3-disubstituted thioester adducts (69% yield, syn:anti 13:1, 90% ee). To the best of applicants' knowledge, this transformation represents the first known example of an asymmetric catalytic Mukaiyama-Michael reaction using α,β-unsaturated aldehydes. Indeed, the use of chiral Lewis acids with these substrates has traditionally lead to the production of Mukaiyama aldol adducts (see Maruoka et al. (1994) *J. Am. Chem. Soc.* 116 :4131–4132). In addition, the catalysts of the invention are effective in facilitating the addition of 1,3-dicarbonyl or 1,3-ketosulfone systems in an asymmetric Michael reaction; see Equation 12 and Example 11. The reaction does not require the pregeneration of a masked enolate equivalent, as the equilibrium content of enol tautomer in 1,3-dicarbonyl or 1,3-ketosulfone substrates is sufficient to ensure 1,4-conjugate addition to the activated iminium ion intermediate

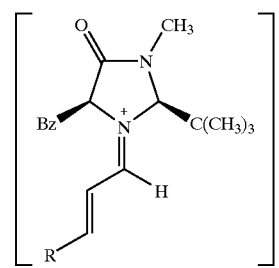

formed from catalyst (1) and the α,β-unsaturated aldehyde

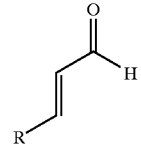

As established in Example 11, the addition of cyclohexanedione to cinnamaldehyde can be mediated with good reaction efficiency and enantiocontrol (70% yield, 84% ee) using a catalyst of the invention.

Of particular interest is the use of the present catalysts and methods in the alkylation of bicyclic and polycyclic compounds containing at least one N-heterocyclic ring, as indicated above with respect to the alkylation of indoles. In this embodiment, the bicyclic or polycyclic compound, such as (IV)

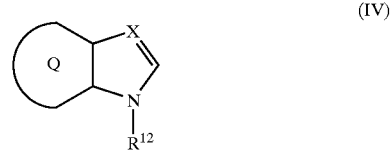

(IV)

undergoes reaction with the α,β-unsaturated aldehyde in the presence of a catalyst of the invention i.e., having the structure of formula (IIA) or (IIB). In formula (IV):

$R^{12}$ is selected from the group consisting of hydrogen, hydrocarbyl, substituted hydrocarbyl, heteroatom-containing hydrocarbyl, and substituted heteroatom-containing hydrocarbyl, and is preferably selected from the group consisting of hydrogen, $C_1$–$C_{12}$ alkyl, $C_1$–$C_{12}$ alkenyl, $C_5$–$C_{20}$ aryl, and $C_5$–$C_{20}$ aralkyl.

Q is a five- or six-membered aromatic ring containing zero to 3 heteroatoms selected from N, O and S and zero to 4 nonhydrogen substituents, wherein any two adjacent nonhydrogen substituents may together form an additional aryl, substituted aryl, heteroaryl, or heteroaryl substituent. In a preferred embodiment, Q is phenyl substituted with zero to 2 nonhydrogen substituents selected from the group consisting of $C_1$–$C_{12}$ alkyl, $C_1$–$C_{12}$ alkoxy, and halo.

X is N or $CR^{13}$ wherein $R^{13}$ is hydrogen, hydrocarbyl, substituted hydrocarbyl, heteroatom-containing hydrocarbyl, or substituted heteroatom-containing hydrocarbyl. Preferably, X is $CR^{13}$.

For example, the aforementioned method may involve the enantioselective alkylation of an indole at the 3-position thereof, wherein (a) an indole reactant selected from the group consisting of unsubstituted indole and indole substituted at the 1-, 4-, 5-, 6-, and/or 7-positions with a nonhydrogen substituent, is contacted with (b) an α,β-unsaturated aldehyde in the presence of (c) a catalyst of the invention. If the indole reactant is substituted, preferred such reactants are substituted at the 1-position (i.e., at the nitrogen of the pyrrole ring) with $C_1$–$C_{12}$ alkyl, $C_1$–$C_{12}$ alkenyl, $C_5$–$C_{20}$ aryl, or $C_5$–$C_{20}$ aralkyl, and/or substituted at the 4-, 5-, 6- and/or 7-positions with a $C_1$–$C_{12}$ alkyl, $C_1$–$C_{12}$ alkoxy, or halo substituent. Preferred indole reactants have the structure of formula (V)

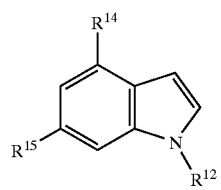

(V)

wherein $R^{12}$ is as defined above, and $R^{14}$ and $R^{15}$ are independently selected from the group consisting of hydrogen, $C_1$–$C_{12}$ alkyl, $C_1$–$C_{12}$ alkoxy, and halo. Use of the catalysts and methods of the invention in the alkylation of indoles is schematically illustrated in FIG. 2.

In a specific and particularly preferred embodiment, X of the bicyclic or polycyclic compound (IV) undergoing an alkylation reaction with the α,β-unsaturated aldehyde is $CR^{13}$ wherein $R^{13}$ is —$L^1$—Nu:, in which $L^1$ is a hydrocarbylene, substituted hydrocarbylene, heteroatom-containing hydrocarbylene, or substituted heteroatom-containing hydrocarbylene linker with 2 to 6 atoms in the linker backbone, and Nu: is a nucleophilic group capable of addition to an unsaturated bond, e.g., secondary amino, hydroxyl, or sulfhydryl, with secondary amino groups (including —NH-Prot wherein Prot is an amine protecting group such as butyloxycarbonyl, or "BOC") most preferred. Generally, $L^1$ is substituted or unsubstituted $C_2$–$C_6$ alkylene, and more preferably is $C_2$–$C_4$ alkylene (e.g., ethylene). The —$L^1$—Nu: substituent allows for a subsequent reaction step in which Nu: adds to the double bond of the pyrrole ring. This cycloaddition step, following the initial reaction of compound (IV) with the α,β-unsaturated aldehyde, enables the straightforward synthesis of a host of useful polycyclic compounds. Such polycyclic compounds include, by way of example, pyrroloindolines. Use of the catalysts and methods of the invention in organocatalytic pyrroloindoline alkylation is schematically illustrated in FIG. 3.

Accordingly, in a further embodiment, the invention pertains to a method for synthesizing a pyrroloindoline having the structure of formula (VII)

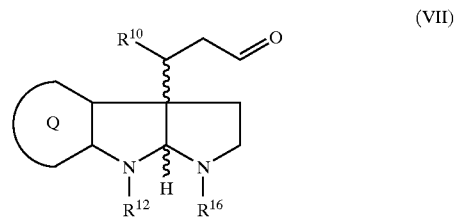

(VII)

wherein $R^{10}$ is selected from the group consisting of hydrogen, $C_1$–$C_{30}$ hydrocarbyl, heteroatom-containing $C_1$–$C_{30}$ hydrocarbyl, substituted $C_1$–$C_{30}$ hydrocarbyl, substituted heteroatom-containing $C_1$–$C_{30}$ hydrocarbyl, and functional groups, $R^{12}$ and Q are as defined previously, and $R^{16}$ is hydrocarbyl, substituted hydrocarbyl, heteroatom-containing hydrocarbyl, or substituted heteroatom-containing hydrocarbyl. The method involves contacting a reactant having the structure of formula (VIII)

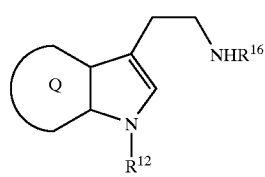

(VIII)

with an α,β-unsaturated aldehyde having the structure (IX)

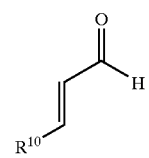

(IX)

in the presence of a catalyst of the invention, i.e., a compound having the structure of formula (IIA) or (IIB). When the catalyst has the structure of formula (IIA), the pyrroloindoline product will have the structure of formula (VIIA)

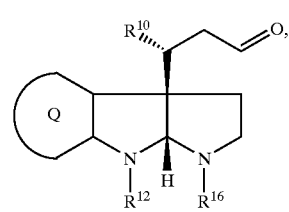

(VIIA)

while when the catalyst has the structure of formula (IIB), the pyrroloindoline product will have the structure of formula (VIIB)

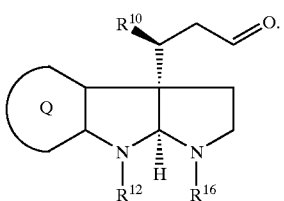

(VIIB)

FIG. 4 schematically illustrates the synthesis of a pyrroloindoline "core" (3-(8-allyl-1-butyloxycarbonyl-2,3,8,8a-tetrahydro-1H-pyrrolo[2,3-b]indol-3a-yl)-propionaldehyde) from N-protected (i.e., butyloxycarbonyl-protected) 2-(1-allyl-1H-indol-3-yl)-ethylamine using a catalyst of the invention, i.e., the p-toluenesulfonic acid salt of (1). As also illustrated in FIG. 4, the utility of the general method for synthesizing the pyrroloindoline core may be readily extrapolated to the synthesis of a natural product such as (+)-flustramine B. FIG. 5 illustrates the molecular structures of other natural products that can be attained using the aforementioned methodology.

The foregoing reactions are intended to be illustrative and not in any way limiting of the reactions with which the present catalysts and methods are useful. That is, the imidazolidinones of the invention are useful to catalyze a host of reactions and reaction types, of which those disclosed herein are merely representative.

Any of the reactions herein, including both preparation and use of the imidazolidinone salt, can be carried out on a solid support, using solid phase synthesis techniques. Solid-phase synthesis enables synthesis and use of the imidazolidinone salt in combinatorial chemistry processes, wherein an array or "matrix" of reactions are conducted in parallel on a single substrate. In such a case, the imidazolidinone itself (or the anion X⁻ with which the cationic imidazolidinone is associated) can be bound either directly or indirectly to the surface of a solid substrate, if indirectly, through a cleavable or noncleavable linker. For example, the imidazolidinone can be linked to the surface of a substrate through any of $R^1$ through $R^5$. Any solid support may be used. Typical substrates are those conventionally used in solid phase chemistry and which allow for chemical synthesis thereon. The only limitation upon the materials useful for constructing substrates is that they must be compatible with the reaction conditions to which they are exposed. Suitable substrates useful in practicing the methods of the invention include, but are not limited to, organic and inorganic polymers (e.g., polyethylene, polypropylene, polystyrene, polytetrafluoroethylene), metal oxides (e.g., silica, alumina), mixed metal oxides, metal halides (e.g., magnesium chloride), minerals, quartz, zeolites, and the like. Other substrate materials will be apparent to those of skill in the art.

Process conditions: The catalytic reactions of the invention are preferably although not necessarily carried out in water, organic solvents or ionic liquids, i.e., in any solvent that allows retention and regeneration of the catalyst composition and removal of the reaction product following completion of the reaction. The reactions may be carried out in batch, semi-continuously or continuously, in air or an inert atmosphere, at autogenous pressure or higher, depending, for example, on the nature of the catalyst composition and reactants used. The reaction temperature will generally be in the range of about −100° C. to 100° C., preferably in the range of about −90° C. to 50° C. The amount of catalyst (i.e., either an acid addition salt of the imidazolidinone, or a mixture of the imidazolidinone and an acid co-catalyst) is generally in the range of 1 mole % to 1 stoichiometric equivalent, and the molar ratio of the α,β-unsaturated aldehyde to the second reactant is generally in the range of about 100:1 to 1:100, preferably in the range of about 10:1 to 1:10. Industrially, the reaction may be scaled up to 10,000 gallons or more. Catalysis may be heterogeneous or homogeneous. It will be appreciated by those skilled in the art of catalysis that the aforementioned process conditions may vary depending on the particular reaction, the desired product, the equipment used, and the like. Generally, the reaction product is obtained after completion of the reaction, wherein an optional extraction and/or catalyst recovery step and/or drying is followed by concentration or distillation to give the crude product and purification, e.g., by chromatography, sublimation, precipitation, extraction, crystallization with optional seeding and/or co-crystallization aids.

It is to be understood that while the invention has been described in conjunction with the preferred specific embodiments thereof, that the description above as well as the examples that follow are intended to illustrate and not limit the scope of the invention. Other aspects, advantages and modifications within the scope of the invention will be apparent to those skilled in the art to which the invention pertains.

All patents, patent applications, journal articles and other reference cited herein are incorporated by reference in their entireties.

Experimental

In the following examples, efforts have been made to ensure accuracy with respect to numbers used (e.g., amounts, temperature, etc.) but some experimental error and deviation should be accounted for. Unless indicated otherwise, temperature is in degrees C and pressure is at or near atmospheric.

Commercial reagents were purified prior to use following the guidelines of Perrin and Armarego, *Purification of Laboratory Chemicals*, Fourth Edition (Oxford, Butterworth-Heinemann, 1996). Organic solutions were concentrated under reduced pressure on a Büchi rotary evaporator. Methylene chloride was distilled from calcium hydride prior to use. Tetrahydrofuran was distilled from sodium benzophenone ketyl prior to use. Chloroform was distilled from calcium sulfate and potassium carbonate and passed through an alumina plug prior to use. Chromatographic purification of products was accomplished using forced-flow chromatography on ICN 60 32–64 mesh silica gel 63 according to the method of Still et al. (1978) *J. Org. Chem.* 43:2923. Thin-layer chromatography (TLC) was performed on EM Reagents 0.25 mm silica gel 60-F plates. Visualization of the developed chromatogram was performed by fluorescence quenching or p-anisaldehyde stain.

$^1$H and $^{13}$C NMR spectra were recorded on Varian Mercury 300 spectrometers (300 MHz and 75 MHz respectively) as noted, and are internally referenced to residual protio solvent signals. Data for $^1$H NMR are reported as follows: chemical shift (δ ppm), multiplicity (s=singlet, d=doublet, t=triplet, q=quartet, m=multiplet, br=broad), coupling constant (Hz), integration and assignment. Data for $^{13}$C NMR are reported in terms of chemical shift (ppm). IR spectra were recorded on a Perkin Elmer Paragon 1000 spectrometer and are reported in terms of frequency of absorption (cm$^{-1}$). Mass spectra were obtained from the UC Irvine Mass Spectral facility. Gas liquid chromatography (GLC) was performed on Hewlett-Packard 6850 and 6890 Series gas chromatographs equipped with a split-mode capillary injec-

EXAMPLE 1

Catalyst Preparation

This example describes the synthesis of a catalyst of the invention in two steps from phenylalanine methyl ester, according to the following scheme:

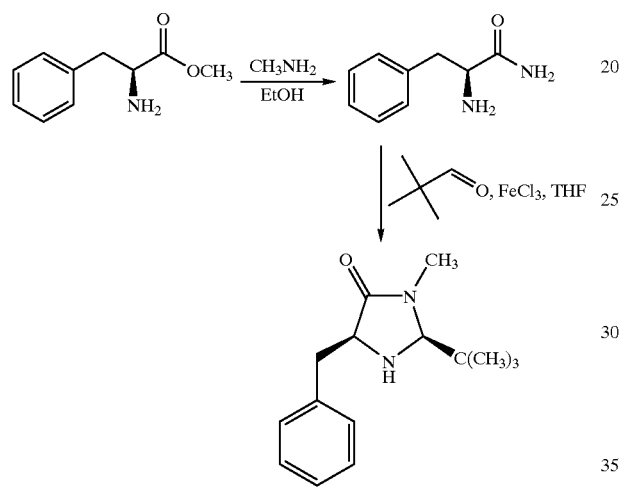

Hydrochloride salt of (2S,5S)-5-benzyl-2-tert-butyl-3-methylimidazolidin-4-one (1): To a solution of ethanolic MeNH$_2$ (8.0 M, 50 ml) was added (S)-phenylalanine methyl ester (23.0 g, 130 mmol). The resulting solution was stirred at room temperature until the amino ester was judged to be consumed by TLC analysis. The resulting solution was then concentrated to provide (S)-phenylalanine N-methyl amide (18 g, 82% yield) as a white solid. To a flask containing (S)-phenylalanine N-methyl amide (8.9 g, 50 mmol) was added THF (100 ml), trimethylacetaldehyde (5.4 g, 50 mmol), FeCl$_3$ (1.7 g, 10 mmol) and 4 Å MS (5.0 g). The resulting mixture was stirred at room temperature for 36 h, then washed with H$_2$O (3×100 mL). The combined organics were concentrated and the resulting residue was treated with HCl (27 mL, 1N in ether). The resulting heterogeneous mixture was filtered to removed the undesired trans isomer. HCl salt and the resulting solution was concentrated. The residue was recrystallized (9:1 pentane/CH$_2$Cl$_2$) to provide the product (1) as a crystalline solid (2.88 g, 23% yield, >99% ee). IR (film) 3343, 2958, 1605, 1028 cm$^{-1}$; $^1$H NMR (300 MHz, CDCl$_3$) δ 7.31–7.17 (m, 5H, ArH), 4.04 (s, 1H, NCHN), 3.72–3.65 (m, 1H, CHCH$_2$), 3.13 (dd, J=4.1, 13.7 Hz, 1H, CH$_2$), 2.92 (dd, J=7.7, 13.7 Hz, 1H, CH$_2$), 2.90 (s, 3H, NCH$_3$), 0.82 (s, 9H, C(CH$_3$)$_3$); $^{13}$C NMR (75 MHz, CDCl$_3$) δ 175.3, 138.0, 129.8, 128.7, 126.8, 82.7, 77.8, 77.4, 76.9, 59.7, 38.6, 35.4, 31.0, 25.7; [α]$_D$=−39.6 (c=1.0, CHCl$_3$). The enantiomeric ratio was determined by HPLC using a Chiralpak OD-H and OD guard column (3.0% i-PrOH/hexanes, 1 mL/min); (5S) isomer t$_r$=16.7 min, (5R) isomer t$_r$=20.1 min.

The trans (2R,5S) isomer of catalyst (1) can be converted to the desired cis (2S,5S) isomer as follows: A solution of trans-(2R,5S)-5-benzyl-2-tert-butyl-3-methylimidazolidin-4-one.HCl salt (6.0 g, 27.9 mmol) in Et$_2$O (100 mL) was washed with saturated aqueous NaHCO$_3$ (100 mL) before the organics were separated and concentrated. To a flask containing the resulting residue was added THF (50 ml) and FeCl$_3$ (0.95 g, 5.6 mmol). The resulting solution was maintained at room temperature for 14 h, then washed with H$_2$O (3×50 mL). The combined organics were concentrated and the resulting residue was treated with HCl (13 mL, 1N in ether). The resulting heterogeneous mixture was filtered to removed the undesired trans isomer.HCl salt and the resulting solution was concentrated. The residue was recrystallized (9:1 pentane/CH$_2$Cl$_2$) to provide the product as a crystalline solid (1.65 g, 22% yield, >99% ee).

It will be appreciated that the foregoing method can be readily adapted for the synthesis of analogous catalysts, i.e., imidazolidinones encompassed by formulae (IIA) and (IIB), by using appropriately substituted reactants as starting materials.

Examples 2–12 describe the use of (1) as a catalyst for a variety of reactions involving α,β-unsaturated aldehydes as reactants.

EXAMPLE 2

Representative Intermolecular Diels-Alder Reaction

This example describes a Diels-Alder reaction of (E)-crotonaldehyde and cyclopentadiene, catalyzed by (1), to provide (1S,2R,3S,4R)-3-methylbicyclo[2.2.1]hex-5-ene-2-carboxaldehyde:

To a solution of (2S,5S)-5-benzyl-2-tert-butyl-3-methylimidazolidin-4-one (1) (24.6 mg, 0.100 mmol) in 1.0 mL CHCl$_3$ was added HCl (25 μL, 4 M solution in dioxane, 0.10 mmol), followed by (E)-crotonaldehyde (82.8 μL, 1.00 mmol). After stirring for five minutes at room temperature, the solution was cooled to −60° C. and cyclopentadiene (330 μL, 4.0 mmol), pre-cooled to −60° C., was added. The reaction was allowed to stir for 4.5 days after which time the solution was purified directly by gel silica chromatography (3:97 Et$_2$O/pentane to afford the product as a colorless oil (108.8 mg, 80% yield, 5.0:1.0 exo:endo; exo 93% ee). Product ratios were determined by GLC with an ASTEC Γ-TA column (50° C., 2° C./min gradient, 23 psi); (1S,2R, 3S,4R) exo isomer t$_r$=22.4 min, (1R,2S,3R,4S) exo isomer t$_r$=22.9 min. $^1$H NMR, $^{13}$C NMR, IR, chiral GLC data for the exo isomer were consistent with previously reported values (Ahrendt et al. (2000) *J. Am. Chem. Soc.* 122:4243–4244).

EXAMPLE 3

Representative Intramolecular Diels-Alder Reaction

This example describes an intramolecular Diels-Alder reaction of 10-phenyl-deca-2,7,9-trienal, catalyzed by the trifluoroacetic acid salt of (1), to provide (3S,4R,5S,7R)-5-phenyl-2,3,3,4,5,7-hexahydro-1H-indene-4-carbaldehyde.

A 2-dram vial equipped with a magnetic stir bar and charged with 10-phenyl-deca-2,7,9-trienal (50 mg, 0.22 mmol) was cooled to −20° C. A solution of (2S,5S)-5-benzyl-2-tert-butyl-3-methylimidazolidin-4-one (10 mg, 0.044 mmol) and trifluoroacetic acid (TFA) (3.4 μL, 0.044 mmol) in CH$_3$CN (0.44 mL), precooled to −20° C., was added. After stirring for 15 h at −20° C., the reaction was determined to be complete by TLC. The crude reaction mixture was warmed to room temperature and then passed directly onto a silica gel column and eluted with EtOAc/hexanes (10:90) to afford the product (42.5 mg, 85% yield, 11:1 endo:endo epimer, endo 93% ee). IR (film) 2952, 2869, 1719, 1640, 1492, 1452,913,744 cm$^{-1}$; $^1$H NMR (300 MHz, CDCl$_3$) 67 9.05 (d, J=4.1 Hz, 1H, CHO), 7.32–7.18 (m, 5H, ArH), 6.14 (d, J=10.1 Hz, 1H, C$_1$—H), 5.59 (m, 1H, C$_2$—H), 4.00 (br, 1H, C$_3$—H), 2.69 (m, 1H, C$_4$—H), 2.04–1.78 (m, 4H), 1.34–1.25 (m, 3H), 1.08 (m, 1H); $^{13}$C NMR (300 MHz, CDCl$_{13}$) 67 205.1, 151.8, 139.8, 131.0, 129.8, 128.7, 127.3, 57.1, 44.8, 44.2, 39.0, 28.9, 27.6, 22.8; HRMS (El) exact mass calcd for C$_{16}$H$_{18}$O (M$^-$) requires m/z 226.1358, found m/z 226.1353. [α]$_D$=+4.35 (c=1.0, CHCl$_3$). The enantiomeric ratio was determined by GLC with an ASTEC β-DM column (122° C. isotherm for 50 min followed by 5° C./min gradient, 1 mL/min); (3S,4R,5S,7R) isomer t$_r$=55.80, (3R,4S,5R,7S) isomer t$_r$=56.20.

EXAMPLE 4

Representative Nitrone Cycloaddition Reaction

This example describes a nitrone cycloaddition reaction catalyzed by the trifluoromethanesulfonic acid salt of (1), to provide (3R,4S,5R)-2-benzyl-4-formyl-5-methyl-3-phenyl-isoxazolidine.

(Z)-N-Benzylidenebenzylamine N-oxide (28.5 mg, 0.135 mmol) and (2S,5S)-5-benzyl-2-tert-butyl-3-methylimidazolidin-4-one (6.7 mg, 0.027 mmol) were dissolved in CHCl$_3$ (1.35 mL). Trifluoromethanesulfonic acid (TfOH) (2.4 μL, 0.027 mmol) was added, and the solution was cooled to −26° C. (E)-Crotonaldehyde (44.7 μL, 0.846 mmol) which had been pre-cooled to −26° C. was added, and the reaction was allowed to stir at −26° C. for 10.5 h, after which time the reaction was judged to be complete by TLC analysis. The mixture was flushed through a plug of silica gel with CH$_2$Cl$_2$. Removal of the solvent in vacuo provided the product as a colorless oil (36.5 mg, 96% yield, endo:exo, 150:1; endo 98% ee.). $^1$H NMR, $^{13}$C NMR and IR data for the endo isomer were consistent with previously reported values (Jen et al. (2000) *J. Am. Chem. Soc.* 122:9874–9875). Diastereomeric and enantiomeric ratios were determined by HPLC analysis of the corresponding alcohol, obtained by NaBH$_4$ reduction of the product aldehyde, with a Chiralcel OD-H column and OD guard column (2.0% i-PrOH/hexanes, 1 mL/min); (3R,4S,5R) isomer t$_r$=33.8 min, (3S,4R,5S) isomer t$_r$=38.4 min, exo isomers t$_r$=20.5 and 22.7 min.

EXAMPLE 5

Representative Friedel-Crafts Alkylation

This example describes a Friedel-Crafts alkylation reaction of 1-phenyl-pyrrolidine and 4-oxo-butenoic acid methyl ester, catalyzed by the hydrochloride salt of (1), to provide (R)-4-oxo-2-(4-pyrrolidin-1-yl-phenyl)-butyric acid methyl ester.

To an amber 2-dram vial equipped with a magnetic stir bar was added (2S, 5s)-5-benzyl-2-tert-butyl-3-methylimidazolidin-4-one (12.3 mg, 0.0500 mmol), 4-oxobutenoic acid methyl ester (57.1 mg, 0.500 mmol), CHCl$_3$ (0.5 ml), HCl (4M in dioxane, 12.5 μL, 0.0500 mmol), and 1-phenylpyrrolidine (144 μL, 1.00 mol). The solution was stirred for 20 min at ambient temperature and loaded directly on a column of silica gel for purification. Gradient elution with EtOAc/hexanes (20:80 to 40:60) afforded the product as a white powder (126 mg, 96% yield, 95% ee). IR (film) 2974.5, 2959, 2899, 2827, 2726, 1730, 1718, 1614, 1522, 1488, 1435, 1374, 1229, 1164, 1091, 814, 771, 531 cm$^{-1}$; $^1$H NMR (300 MHz, CDCl$_3$) δ 9.75 (s, 1H, CHO), 7.12 (d, J=8.8 Hz, 2H, ArH), 6.51 (d, J=8.8 Hz, 2H, ArH), 4.02 (dd, J=4.7, 9.6 Hz, 1H, ArCH), 3.65 (s, 3H, OCH$_3$), 3.33 (dd, J=9.9, 18.4 Hz, 1H, CH$_2$CO), 3.28–3.23 (m, 4H, N(CH$_2$)$_2$), 2.76 (dd, J=5.0, 18.4 Hz, 1H, CH$_2$CO), 2.01–1.96 (m, 4H, CH$_2$CH$_2$CH$_2$CH$_2$); $^{13}$C NMR (75 MHz, CDCl$_3$) δ 200.5, 174.2, 147.6, 128.7, 124.1, 112.1, 52.5, 47.8, 47.7, 44.2, 25.7. [α]$_D$=−147.8 (c=1.0, CHCl$_3$). The enantiomeric ratio of the product was determined by HPLC analysis of the corresponding alcohol (obtained by NaBH$_4$ reduction) using a Chiralpak AD and AD guard column (10% ethanol/hexanes, 1 mL/min); S isomer t$_r$=20.9 min, R isomer t$_r$=24.4 mm.

EXAMPLE 6

Representative Pyrrole Alkylation

This example describes the alkylation of pyrrole with 4-oxo-2-butenyl benzoate, catalyzed by the chloroacetic acid salt of (1), to provide (R)-4-hydroxy-2-(1H-pyrrol-2-yl)-butyl benzoate.

To a 2-dram vial equipped with a magnetic stir bar and charged with (2S,5S)-5-benzyl-2-tert-butyl-3-methylimidazolidin-4-one.ClCH$_2$CO$_2$H (CCA) (49.5 mg, 0.15 mmol) was added diethyl ether (1.10 mL) and H$_2$O (0.15 mL). The solution was cooled to −28° C. and stirred 5 min before the addition of pyrrole (0.25 mL, 3.63 mmol). After an additional 5 min, 4-oxo-2-butenyl benzoate (138.0 mg, 0.73 mmol) in diethyl ether (0.25 mL) was added dropwise over the course of two minutes. After 36 h the reaction was judged to be complete by TLC analysis. The reaction mixture was transferred cold into a 50 mL flask containing NaBH$_4$ (118.4 mg, 0.79 mmol) in ethanol (10.0 mL). After 15 min the solution was treated with saturated aqueous NaHCO$_3$, and the resulting mixture was extracted into CH$_2$Cl$_2$ (3×10 mL). The combined organic layers were washed with saturated aqueous NaHCO$_3$ and brine, dried (MgSO$_4$) and concentrated. The resulting residue was purified by silica gel chromatography (40:60 EtOAc/hexanes) to afford the product as a white solid (157.1 mg, 83% yield, 90% ee). IR (film) 3485, 2957, 1699, 1651, 1454, 1277, 1177, 1120, 1070, 1027, 711.6 cm$^{-1}$; $^1$H NMR (300 MHz, CDCl$_3$) δ 8.46 (br s, 1H, NH), 8.06–7.98 (m, 2H, ArH), 7.62–7.54 (tt, J=1.2, 7.8 Hz, 1H, ArH), 7.50–7.42 (m, 2H ArH), 6.74–6.70 (m, J=1.8, 2.7 Hz, 1H, ArH), 6.20–6.14 (dd, J=2.7, 6.0 Hz, 1H, ArH), 6.06 (t, 1H, J=3.6 Hz, ArH), 4.58–4.50 (m, 1H, BzOCH$_2$), 4.50–4.42 (m, 1H, BzOCH$_2$), 3.84–3.72 (m, CH$_2$OH, 1H), 3.72–3.62 (m, CH$_2$OH, 1H), 3.44–3.32 (m, BzOCH$_2$CH, 1H), 2.16–2.02 (m, CH$_2$CH$_2$OH, 1H), 2.02–1.86 (m, CH$_2$CH$_2$OH, 1H), 1.48 (br, s, OH, 1H); $^{13}$C NMR (75 MHz, CDCl$_3$) δ 133.3, 131.6, 130.2, 129.7, 128.6, 117.2, 108.5, 105.4, 68.4, 60.8, 35.3, 34.5; [α]$_D$=−20.2 (c=1.0, CHCl$_3$). Product ratio was determined by HPLC with a Chiralpak AD column and AD guard (10% i-PrOH/hexanes, 1 mL/min); S isomer t$_r$=18.8 min, R isomer t$_r$=20.4 min.

EXAMPLE 7

Representative in Dole Alkylation

This example describes the alkylation of 1-methyl-1H-indole with (E)-crotonaldehyde, catalyzed by the trifluoroacetic acid salt of (1), to provide (R)-3-(1-methyl-1H-indol-3-yl)-butanal.

To an amber 2-dram vial equipped with a magnetic stir bar and charged with (2S,5S)-5-benzyl-2-tert-butyl-3-methylimidazolidin-4-one (24.6 mg, 0.10 mmol) was added $CH_2Cl_2$ (0.85 mL), i-PrOH (0.15 mL) and trifluoroacetic acid (7.7 µL, 0.10 mmol). The solution was placed in a bath at −83° C. and stirred for 5 min before the addition of (E)-crotonaldehyde (125 µL, 1.50 mmol). After stirring for an additional 10 minutes, 1-methyl-1H-indole (64 µL, 0.50 mmol) was added in one portion. The resulting suspension was stirred at −83° C. for 19 h. The reaction mixture was then transferred cold through a silica gel plug with $Et_2O$ and concentrated in vacuo. The resulting residue was purified by silica gel chromatography (benzene) to provide the product as a colorless oil (83 mg, 82% yield, 92% ee). IR (film) 3054, 2960, 2824, 2722, 1720, 1616, 1550, 1474, 1374, 1329, 1241, 740 cm$^{-1}$; $^1$H NMR (300 MHz, CDCl$_3$) δ 9.75 (dd, J=2.1, 2.1 Hz, 1H, CHO), 7.63 (d, J=7.8 Hz, 1H, ArH), 7.32–7.21 (m, 2H, ArH), 7.12 (ddd, J=1.5, 7.4, 8.1 Hz, 1H, ArH), 6.84 (s, 1H, NCH), 3.75 (s, 3H, NCH$_3$), 3.68 (dt, J=6.9, 13.8 Hz, 1H, ArCH), 2.88 (ddd, J=2.7, 6.9, 16.2 Hz, 1H, CH$_2$CO); 2.71 (ddd, J=2.7, 6.9, 16.2 Hz, 1H, CH$_2$CO); 1.44 (d, J=7.2 Hz, 3H, CHCH$_3$); $^{13}$C NMR (75 MHz, CDCl$_3$) δ 202.8, 137.2, 126.6, 125.2, 121.8, 119.1, 118.9, 118.8, 109.5, 51.2, 32.8, 26.0, 21.9; HRMS (CI) exact mass calcd for (C$_{13}$H$_{15}$NO) requires m/z 201.1154, found m/z 201.1152. [α]$_D$=4.2 (c=1.0, CHCl$_3$). The enantiomeric ratio was determined by HPLC analysis of the alcohol, obtained by NaBH$_4$ reduction of the product aldehyde, using a Chiralpak AD and AD guard column (2.0% ethanol/hexanes, 1 mL/min); S isomer t$_r$=25.2 min, R isomer t$_r$=27.8 min.

EXAMPLE 8

Representative Furan Alkylation

This example describes the alkylation of 2-methoxyfuran with (E)-crotonaldehyde, catalyzed by the dichloroacetic acid salt of (1), to provide (R)-3-(5-methoxyfuran-2-yl)-butyraldehyde.

To a 2-dram vial equipped with a magnetic stir bar and charged with (2S,5S)-5-benzyl-2-tert-butyl-3-methylimidazolidin-4-one (24.6 mg, 0.100 mmol) was added CHCl$_3$ (4.00 mL), dichloroacetic acid (DCA) (8.2 µL, 0.10 mmol) and (E)-crotonaldehyde (250 µL, 3.00 mmol). The solution cooled to −40° C. and stirred for 10 min before the addition of 2-methoxyfuran (92 µL, 1.00 mmol) in one portion. After stirring at −40° C. for 5 h, the reaction mixture was then transferred cold through a silica gel plug with $Et_2O$ and concentrated in vacuo. The resulting residue was purified by silica gel chromatography (10% Et$_2$O/petroleum ether) to provide the product as a colorless oil (131.3 mg, 78% yield, 95% ee). IR (film) 2973, 2937, 2837, 2726, 1725, 1617, 1589, 1458, 1438, 1385, 1341, 1261, 1227, 1177, 1054, 1017, 966.2, 942.4, 819.4, 744.0 cm$^{-1}$; $^1$H NMR (300 MHz, CDCl$_3$) δ 9.73 (t, J=2.2 Hz, 1H, CHO), 5.85 (dd, J=2.8, 3.3 Hz, 1H, ArH), 4.99 (d, J=3.0 Hz, 1H, ArH), 3.79 (s, 3H, OCH$_3$), 3.30 (sextet, J=0.8, 1H, CHCH$_3$), 2.74 (ddd, J=2.2, 6.6, 17.0 Hz, 1H, CH$_2$), 2.52 (ddd, J=2.2, 7.1, 17.0 Hz, 1H, CH$_2$); 1.25 (d, J=6.9 Hz, 3H, CHCH$_3$); $^{13}$C NMR (75 MHz, CDCl$_3$) δ 201.7, 160.8, 148.0, 105.4, 79.5, 57.9, 49.3, 28.1, 19.2; HRMS (CI) exact mass calcd for C$_9$H$_{12}$O$_3$) requires m/z 168.0786, found m/z 168.0792. [α]$_D$=−1.7 (c=1.0, CHCl$_3$). The enantiomeric ratio was determined by GLC using an ASTEC Chiraldex Γ-TA column (80° C. isotherm, 1 mL/min); S isomer t$_r$=79.3 min, R isomer t$_r$=80.8 min.

EXAMPLE 9

Representative Thiophene Alkylation

This example describes the alkylation of 2-methoxythiophene with (E)-crotonaldehyde, catalyzed by the trifluoroacetic acid salt of (1), to provide (R)-3-(5-methoxythiophen-2-yl)-butyraldehyde.

To a 2-dram vial equipped with a magnetic stir bar and charged with (2S,5S)-5-benzyl-2-tert-butyl-3-methylimidazolidin-4-one (24.6 mg, 0.100 mmol) was added CHCl$_3$ (2.00 mL), trifluoroacetic acid (7.7 µL, 0.10 mmol) and (E)-crotonaldehyde (250 µL, 3.00 mmol). The solution cooled to −30° C. and stirred for 10 min before the addition of 2-methoxythiophene (101 µL, 1.00 mmol) in one portion. After stirring at −30° C. for 23 h, the reaction mixture was transferred cold through a silica gel plug with Et$_2$O and concentrated in vacuo. The resulting residue was purified by silica gel chromatography (10% Et$_2$O/petroleum ether) to provide the product as a colorless oil (159.6 mg, 87% yield, 92% ee). IR (film) 2963, 2927, 2830, 2724, 1724, 1561, 1510, 1453, 1433, 1408, 1378, 1238, 1206, 1176, 1149, 1106, 1081, 1052, 1025, 995.9, 772.4, 743.8, 715.9 cm$^{-1}$; $^1$H NMR (300 MHz, CDCl$_3$) δ 9.71 (t, J=1.9 Hz, 1H, CHO), 6.40 (dd, J=0.8, 3.8 Hz, 1H, ArH), 5.95 (d, J=3.8 Hz, 1H, ArH), 3.82 (s, 3H, OCH$_3$), 3.30 (sextet, J=7.0, 1H, CHCH$_3$), 2.72 (ddd, J=1.9, 6.9, 16.8 Hz, 1H, CH$_2$), 1.92 (ddd, J=1.9, 7.1 16.8 Hz, 1H, CH$_2$); 1.32 (d, J=6.9 Hz, 3H, CHCH$_3$); $^{13}$C NMR (75 MHz, CDCl$_3$) δ 201.4, 164.4 135.5, 120.3, 102.9, 60.4, 52.3, 30.5, 23.0; HRMS (CI) exact mass calcd for (C$_9$H$_{12}$O$_2$S) requires m/z 184.0558, found m/z 184.0560. [α]$_D$=−13.8 (c=1.0, CHCl$_3$). The enantiomeric ratio was determined by GLC using an ASTEC Chiraldex Γ-TA column (90° C. isotherm, 1 mL/min); S isomer t$_r$=139.5 min, R isomer t$_r$=145.8 min.

EXAMPLE 10

Representative Vinylogous Michael Addition

This example describes a vinylogous Michael addition reaction between 2-(trimethylsilyloxy)furan and (E)-crotonaldehyde, catalyzed by the dichloroacetic acid salt of (1), to provide (3S,2'R)-4-methyl-3-(5-oxo-2,5-dihydrofuran-2-yl)-pentanal.

To a 2-dram vial equipped with a magnetic stir bar and charged with (2S,5S)-5-benzyl-2-tert-butyl-3-methylimidazolidin-4-one (24.6 mg, 0.100 mmol) was added CHCl$_3$ (1.91 mL), H$_2$O (90.0 µL, 5.00 mmol), dichloroacetic acid (DCA) (16.5 µL, 0.20 mmol) and (E)-crotonaldehyde (250 µL, 3.00 mmol). The solution was cooled to −50° C. and stirred for 10 min before the addition of 2-(trimethylsilyloxy)furan (168 µL, 1.00 mmol) in one portion. After stirring at −50° C. for 7 h, the reaction mixture was transferred cold through a silica gel plug with Et$_2$O and concentrated in vacuo. The resulting residue was purified by silica gel chromatography (40% EtOAc/hexanes) to provide the product as a colorless oil (127.2 mg, 70% yield, anti:syn 7.3:1, anti 90% ee). IR (film) 2963, 2870, 2821, 2731, 1753, 1721, 1599, 1467, 1391, 1372, 1325, 1265, 1250, 1163, 1103, 1024, 985.4, 905.2, 819.6 cm$^{-1}$; $^1$H NMR (300 MHz, CDCl$_3$) δ 9.72 (s, 1H, CHO), 7.39 (dd, J=1.4, 5.5 Hz, 1H, CHCO$_2$), 6.10 (dd, J=1.6, 5.8 Hz, 1H, CHCHCHO), 5.22 (m, 1H, OCH), 2.47–2.23 (m, 2H, CH$_2$), 1.97–1.82 (m, 1H, CHMe$_2$), 1.03 (d, J=6.6 Hz, 3H, CH(CH$_3$)$_2$); 0.99 (d, J=6.9 Hz, 3H, CH(CH$_3$)$_2$); $^{13}$C NMR (75 MHz, CDCl$_2$) δ 200.8, 173.1, 156.8, 122.0, 84.0, 40.7, 40.3, 30.4, 20.7, 20.3; HRMS (CI) exact mass calcd for (C$_{10}$H$_{14}$O$_3$) requires m/z 182.0943, found m/z 182.0937. [α]$_D$=−87.4 (c=1.0, CHCl$_3$). The enantiomeric ratio was determined by GLC using an ASTEC Chiraldex B-DM column (170° C. isotherm, 1 mL/min); (3R, 2'S) isomer t$_r$=6.7 min, (3S, 2'R) isomer t$_r$=7.0 min.

EXAMPLE 11

Representative Mukaiyama-Michael Addition

This example describes a representative Mukaiyama-Michael addition reaction, catalyzed by the trichloroacetic acid salt of (1), to provide (2S,3R)-dimethyl-5-oxopentanethioic acid S-isopropyl ester.

To a 2-dram vial equipped with a magnetic stir bar and charged with (2S,5S)-5-benzyl-2-tert-butyl-3-methylimidazolidin-4-one (25 mg, 0.10 mmol) was added EtOAc (0.25 mL), H$_2$O (0.025 mL), trichloroacetic acid (TCA) (16 mg, 0.10 mmol) and (E)-crotonaldehyde (0.125 mL, 1.5 mmol). The solution was stirred for 1 min at room temperature then cooled to −78° C. The solution was stirred for 5 min before addition of tert-butyl-(1-isopropylsulfanyl propenyloxy)-dimethylsilane (0.143 mL, 0.50 mmol). The resulting mixture was stirred −78° C. until consumption of the enolsilane as determined by TLC analysis. The solution was then added to saturated aqueous NH$_4$Cl (2 mL) before being warmed to ambient temperature. The aqueous layer was extracted with Et$_2$O (3×2 mL) and the combined organic extracts were dried (Na$_2$SO$_4$), filtered and concentrated in vacuo. The resulting residue was purified by silica gel chromatography (10:90 EtOAc/hexanes) to afford the product as a colorless oil (70 mg, 69% yield, 13:1 syn:anti, 90% ee). IR (film) 2968, 2932, 2879, 2826, 2722, 1725, 1681, 1455, 1384, 1369,1246, 965, 752 cm$^{-1}$; $^1$H NMR (300 MHz, CDCl$_3$) δ 9.72 (dd, J=2.5, 1.6 Hz, 1H, CHO), 3.62 (septet, J=6.9 Hz, 1H, SCH(Me)$_2$), 2.58–2.38 (m, 2H, CHOCH$_2$), 2.34–2.23 (m, 1H, CHMeCOSiPr), 1.30 (d, J=2.2 Hz, 3H, SCH(CH$_3$)$_2$), 1.28 (d, J=2.2 Hz, 3H, SCH(CH$_3$)$_2$) 1.28–1.24 (m, 1H, CH$_2$CHMeCHMe), 1.14 (d, J=6.9 Hz, 3H, CH(CH$_3$) COSiPr), 0.96 (d, J×6.6 Hz, 3H, CHOCH$_2$CH(CH$_3$)); $^{13}$C NMR (75 MHz, CDCl$_3$) δ 203.0, 201.7, 53.1, 48.8, 34.9, 31.3, 23.3, 23.2, 17.2, 14.5; HRMS (CI) exact mass calcd for (M+1) (C$_{10}$H$_{19}$O$_2$S) requires m/z 203.1106, found m/z 203.1106; [α]$_D$=+32.9 (c=1.0, CHCl$_3$). The diastereomeric ratio was determined by GLC analysis of the product aldehyde using an ASTEC β-DM column (90° C. isotherm, 1 mL/min); syn adduct t$_r$=66.5 min, anti adduct t$_r$=68.2, 71.3 min. The enantiomeric ratio was determined by HPLC analysis of the acyl oxazolidone (after conversion of the product aldehyde to the corresponding acid and coupling with 2-oxazolidone according to previously reported procedures; see Bal et al. (1981) *Tetrahedron* 37:2091–2096, and Evans et al. (2001) *J. Am. Chem. Soc.* 123:4480–4491) using a Chiralcel OD-H and OD guard column (3.0% i-PrOH/hexanes, 1 mL/min); t$_r$=53.3, 60.8 min.

EXAMPLE 12

Representative Michael Addition

This example describes a representative Michael addition reaction between (E)-cinnamaldehyde and 1,3-cyclohexanedione, catalyzed by the hydrochloride salt of (1), to provide (4S)-2-hydroxy-4-phenyl-2,3,4,6,7,8-hexahydro-5H-chromen-5-one.

To a 2-dram vial equipped with a magnetic stir bar and charged with (2S,5S)-5-benzyl-2-tert-butyl-3-methylimidazolidin-4-one (49.3 mg, 0.200 mmol) and 1,3-cyclohexanedione (112 mg, 1.00 mmol) was added CHCT$_3$ (2.0 mL) and HCl (50.0 μL of a 4M soln in dioxane, 0.200 mmol). The solution was cooled to −10° C. and (E)-cinnamaldehyde (250 μL, 2.00 mmol) was added. An additional equivalent of (E)-cinnamaldehyde (125 μL, 1.00 mmol) was added every 12 h for 2 days for a total of 6 equivalents (1.50 mL, 6.00 mmol) of (E)-cinnamaldehyde. After 60 h the solution was passed through a plug of silica gel with Et$_2$O and then concentrated. The crude mixture was purified by silica gel chromatography (50:50 EtOAc/hexanes) to afford the product as a pale yellow solid (171 mg, 70% yield, 84% ee). IR (film) 3329, 2945, 2892, 2248, 1949, 1876, 1808, 1603, 1493, 1453, 1396, 1332, 1156, 1124, 1072, 1022, 976, 919, 832, 732, 702 cm$^{-1}$; $^1$H NMR (300 MHz, CDCl$_3$) δ 7.27–7.22 (m, 2H, ArH), 7.18–7.13 (m, 1H, ArH), 7.19–7.06 (m, 2H, ArH), 5.14 (m, 1H, CHOH), 4.27 (d, J=17.1 Hz, 1H, OH), 4.02 (m, 1H, CHPh), 2.59–2.29 (m, 4H, CH$_2$CH$_2$CH$_2$CO, CH$_2$CO), 2.12–1.89 (m, 4H, CH$_2$CH$_2$CO, CH$_2$CHOH); $^{13}$C (75 MHz, CDCl$_3$) δ 197.5, 171.5, 144.1, 128.6, 127.5, 126.5, 112.6, 93.4, 37.2, 37.0, 34.2, 29.2, 21.3; HRMS (CI) exact mass calcd for (C$_{15}$H$_{16}$O$_3$) requires m/z 244.1099, found m/z 244.1100. [α]$_D$=+63.5 (c=1.0, CHCl$_3$). The enantiomeric ratio was determined by GLC using an ASTEC B-DM column (190° C. isotherm, 1 mL/min); (4S) isomer t$_r$=53.4 min, (4R) isomer t$_r$=55.1 min.

Catalyst Evaluation for Indole Alkylation Reactions

The efficiency and enantioselectivity of various imidazolidinone compounds were evaluated with respect to the alkylation of 1-methyl-1H-indole with (E)-crotonaldehyde. The catalysts evaluated were as follows: (1a), the trifluoroacetate (TFA) salt of (1); (1b), the p-toluenesulfonic acid (p-TSA) salt of (1); (1c), the 2-nitrobenzoic acid (2-NBA) salt of (1); (2a), the trifluoroacetate salt of (5S)-5-benzyl-2,2,3-trimethylimidazolidin-4-one, prepared as described in U.S. Pat. No. 6,307,057 to MacMillan et al.; (2b), the p-toluenesulfonic acid salt of (5S)-5-benzyl-2,2,3-trimethylimidazolidin-4-one, also prepared as described in U.S. Pat. No. 6,307,057; and (2c), the 2-nitrobenzoic acid salt of (5S)-5-benzyl-2,2,3-trimethylimidazolidin-4-one, also prepared as described in U.S. Pat. No. 6,307,057. The reaction conditions and results are shown in Table 1:

TABLE 1

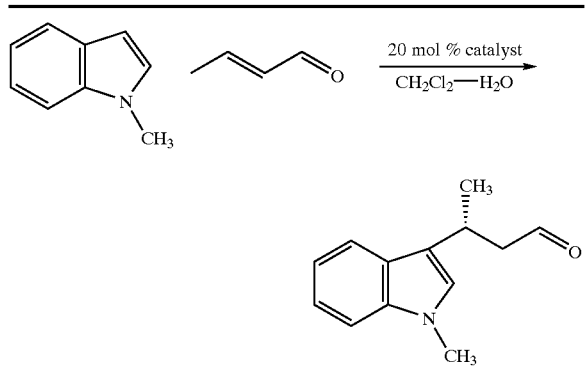

| entry | catalyst | cocatalyst | temp, °C | time (h) | % yield | % ee[a,b] |
|---|---|---|---|---|---|---|
| 1 | 1a | TFA | −40 | 1.5 | 70 | 85 |
| 2 | 1b | p-TSA | −40 | 4 | 98 | 88 |
| 3 | 1c | 2-NBA | −40 | 22 | 88 | 88 |
| 4 | 1b | p-TSA | −83 | 48 | 15 | 80 |
| 5 | 1a | TFA | −83 | 31 | 84 | 92 |
| 6 | 1a | TFA | −83 | 19 | 82 | 92[c] |
| 7 | 2a | TFA | −40 | 48 | 83 | 56 |
| 8 | 2b | p-TSA | −40 | 48 | 8 | 44 |
| 9 | 2c | 2-NBA | −40 | 48 | 79 | 50 |

[a]Product ratios determined by chiral HPLC.
[b]Absolute configuration assigned by chemical correlation to a known compound.
[c]Reaction conducted with $CH_2Cl_2$-i-PrOH (85:15 v/v) as solvent.

As indicated in Table 1, catalysts 2a–2c provided the substituted indole product with only moderate enantioselectivity (56% ee) and relatively poor efficiency (83% yield after 48 h). In contrast, the tert-butyl-benzyl imidazolidinone salts 1a and 1b were successful in affording the benzylic substituted indole in ≧85% ee and ≧70% yield (entries 1 and 2, 20 mol % catalyst, −40° C., 1.5–4 h). An enantioselectivity/temperature profile indicated that optimal enantiocontrol would be available at −83° C. with catalyst 1a (entry 5, 84% yield, 92% ee). A survey of solvent additives revealed that the use of isopropyl alcohol (15% v/v in $CH_2Cl_2$) had a fairly significant influence on reaction rate without loss in enantiocontrol (entry 6, 82% yield, 19 h). Accordingly, the TFA salt 1a was selected as the catalyst for use in the indole alkylation reactions of Examples 13–26.

General procedure for the indole alkylation reactions of Examples 13–24: An amber 2-dram vial equipped with a magnetic stir bar and containing (2S,5S)-5-benzyl-2-tert-butyl-3-methyl-imidazolidin-4-one was charged with $CH_2Cl_2$, isopropanol, and the appropriate acid, then placed in a bath of a desired temperature. The solution was stirred for 5 min before addition of the α,β-unsaturated aldehyde. After stirring for an additional 10 minutes the indole substrate was added in one portion. The resulting suspension was stirred at constant temperature until complete consumption of the indole as determined by TLC. The reaction mixture was then passed cold through a silica gel plug with $Et_2O$ and then concentrated. The resulting residue was purified by silica gel chromatography (solvents noted) to afford the title compounds. The enantioselectivity was determined by subjecting approximately 10 mg of the title compound to an excess of $NaBH_4$ and 1 mL of ethanol. After 15 min, the solution was treated with saturated aqueous $NaHCO_3$, and the mixture was extracted with $CH_2Cl_2$. The organic layer was separated, filtered through a silica gel plug and subjected to chiral HPLC analysis (conditions noted).

EXAMPLE 13

(R)-3-(1-Methyl-1H-indol-3-yl)-butanal (Table 1, entry 6; Table 2, entry 1): Prepared according to the general procedure from (E)-crotonaldehyde (125 μL, 1.50 mmol), 1-methyl-1H-indole (64 μL, 0.50 mmol), TFA (7.7 μL, 0.10 mmol) and (2S,5S)-5-benzyl-2-tert-butyl-3-methyl-imidazolidin-4-one (24.6 mg, 0.100 mmol) in $CH_2Cl_2$ (0.85 mL) and isopropanol (0.15 mL) at −83° C. for 19 h to provide, after silica gel chromatography (benzene), the title compound as a colorless oil (83 mg, 82% yield, 92% ee). IR (film) 3054, 2960, 2824, 2722, 1720, 1616, 1550, 1474, 1374, 1329, 1241, 740 cm$^{-1}$; $^1$H NMR (300 MHz, CDCl$_3$) δ 9.75 (dd, J=2.1, 2.1 Hz, 1H, CHO), 7.63 (d, J=7.8 Hz, 1H, ArH), 7.32–7.21 (m, 2H, ArH), 7.12 (ddd, J=1.5, 7.4, 8.1 Hz, 1H, ArH), 6.84 (s, 1H, NCH), 3.75 (s, 3H, NCH$_3$), 3.68 (dt, J=6.9, 13.8 Hz, 1H, ArCH), 2.88 (ddd, J=2.7, 6.9, 16.2 Hz, 1H, CH$_2$CO); 2.71 (ddd, J=2.7, 6.9, 16.2 Hz, 1H, CH$_2$CO); 1.44 (d, J=7.2 Hz, 3H, CHCH$_3$); $^{13}$C NMR (75 MHz, CDCl$_3$) δ 202.8, 137.2, 126.6 125.2, 121.8, 119.1, 118.9, 118.8, 109.5, 51.2, 32.8, 26.0, 21.9; HRMS (CI) exact mass calcd for (C$_{13}$H$_{15}$NO) requires m/z 201.1154, found m/z 201.1152. [α]$_D$=−4.2 (c=1.0, CHCl$_3$). The enantiomeric ratio was determined by HPLC analysis of the alcohol, obtained by NaBH$_4$ reduction of the aldehyde, using a Chiracel AD and AD guard column (2:98 ethanol/hexanes, 1 mL/min); S isomer t$_r$=25.2 min and R isomer t$_r$=27.8 min.

EXAMPLE 14

(R)-3-(1-Methyl-1H-indol-3-yl)-hexanal (Table 2, entry 2): Prepared according to the general procedure from 2-hexenal (174 μL, 1.50 mmol), 1-methyl-1H-indole (64 μL, 0.50 mmol), TFA (7.7 μL, 0.10 mmol) and (2S,5S)-5-benzyl-2-tert-butyl-3-methyl-imidazolidin-4-one (24.6 mg, 0.100 mmol) in $CH_2Cl_2$ (0.85 mL) and isopropanol (0.15 mL) at −60° C. for 6 h to provide, after silica gel chromatography (5:95 EtOAc/hexanes), the title compound as a colorless oil (92 mg, 80% yield, 93% ee). IR (film) 2959, 2923, 2870, 1720, 1483, 1470, 1425, 1376, 1327, 1244, 1159, 1132, 1016, 734 cm$^{-1}$; $^1$H NMR (300 MHz, CDCl$_3$) δ 9.71 (dd, J=2.1, 2.1 Hz, 1H, CHO), 7.67 (d, J=8.4 Hz, 1H, ArH), 7.35–7.24 (m, 2H, ArH), 7.12 (ddd, J=1.5, 7.2, 8.1 Hz, 1H, ArH), 6.87 (s, 1H, NCH), 3.76 (s, 3H, NCH$_3$), 3.55 (m, 1H, ArCH), 2.83 (m, 2H, CH$_2$CO), 1.79 (m, 2H, CHCH$_2$CH$_2$), 1.34 (dt, J=7.2, 22.8 Hz, 2H, CHCH$_2$CH$_3$), 0.92 (dd, J=7.2, 7.2 Hz, 3H, CH$_2$CH$_3$); $^{13}$C NMR (75 MHz, CDCl$_3$) δ 203.0, 137.2, 127.0, 126.0, 121.6, 119.2, 118.7, 117.0, 109.4, 49.7, 38.5, 32.8, 31.4, 20.8, 14.2; HRMS (CI) exact mass calcd for (C$_{15}$H$_{19}$NO) requires m/z 229.1467, found m/z 229.1464. [α]$_D$=−1.7 (c=1.0, CHCl$_3$). The enantiomeric ratio was determined by HPLC analysis of the alcohol, obtained by NaBH$_4$ reduction of the aldehyde, using a Chiracel AS and AS guard column (2:98 ethanol/hexanes, 1 mL/min); S isomer t$_r$=16.1 min and R isomer t$_r$=18.1 min.

EXAMPLE 15

(S)-4-Methyl-3-(1-methyl-1H-indol-3-yl)-pentanal (Table 2, entry 3). Prepared according to the general procedure from 4-methyl-2-pentenal (175 μL, 1.50 mmol), 1-methyl-1H-indole (64 μL, 0.50 mmol), TFA (7.7 μL, 0.10 mmol) and (2S,5S)-5-benzyl-2-tert-butyl-3-methyl-imidazolidin-4-one (24.6 mg, 0.100 mmol) in $CH_2Cl_2$ (0.90 mL) and isopropanol (0.10 mL) at −50° C. for 32 h to provide, after silica gel chromatography (10:90 EtOAc/hexanes), the title compound as a colorless oil (85 mg, 74% yield, 93% ee). IR (film) 3052, 2958, 2870, 2834, 2716, 1723, 1609, 1546, 1482, 1469, 1423, 1373, 1328, 1246, 1160, 1138, 1015, 743 cm$^{-1}$; $^1$H NMR (300 MHz, CDCl$_3$) δ 9.61 (dd, J=2.4, 2.4 Hz, 1H, CHO), 7.63 (dt, J=0.9, 8.1 Hz, 1H, ArH), 7.33–7.22 (m, 2H, ArH), 7.13 (ddd, J=1.5, 6.9, 8.1 Hz, 1H, ArH), 6.82 (s, 1H, NCH), 3.75 (s, 3H, NCH$_3$), 3.40 (dt, J=6.6, 7.8 Hz, 1H, ArCH), 2.81 (d, J=2.4 Hz, 1H, CH$_2$CO); 2.79 (d, J=2.4 Hz, 1H, CH$_2$CO); 2.10 (ddd, J=6.6, 13.2, 19.8 Hz, 1H, CH(CH$_3$)$_2$, 0.96 (d, J=2.1, 3H, CH(CH$_3$)$_2$), 0.94 (d, J=2.1 Hz, 3H, CH(CH$_3$)$_2$; $^{13}$C NMR (75 MHz, CDCl$_3$) δ 203.4, 137.0, 127.6, 126.7, 121.6, 119.4, 118.8, 115.6, 109.3, 46.1, 38.0, 32.9, 32.9, 20.6, 20.4; HRMS (CI) exact mass calcd for (C$_{15}$H$_{19}$NO) requires m/z 229.1467, found m/z 229.1465. [α]$_D$=+15.8 (c=1.0, CHCl$_3$). The enantiomeric ratio was determined by HPLC analysis of the alcohol, obtained by NaBH$_4$ reduction of the aldehyde, using a Chiracel AS and AS guard column (4% ethanol/hexanes, 1 mL/min); R isomer t$_r$=13.4 min and S isomer t$_r$=16.7 min.

EXAMPLE 16

(S)-3-(1-Methyl-1H-indol-3-yl)-3-phenyl-propanal (Table 2, entry 5): Prepared according to the general procedure from cinnamaldehyde (190 μL, 1.50 mmol), 1-methyl-1H-indole (64 μL, 0.50 mmol), TFA (7.7 μL, 0.10 mmol) and (2S,5S)-5-benzyl-2-tert-butyl-3-imidazolidin-4-one (24.6 mg, 0.100 mmol) in CH$_2$Cl$_2$ (0.85 mL) and isopropanol (0.15 mL) at −55° C. for 45 h to provide, after silica gel chromatography (10:90 EtOAc/hexanes), the title compound as a colorless oil (110 mg, 84% yield, 90% ee). IR (film) 3051, 3026, 2945, 2888, 2822, 2733, 1722, 1616, 1604, 1547, 1474, 1429, 1376, 1331, 1245, 1225, 1156, 1131, 1013, 765, 740, 700 cm$^{-1}$; $^1$H NMR (300 MHz, CDCl$_3$) δ 9.76 (dd, J=2.4, 2.4 Hz, 1H, CHO), 7.43 (dt, J=0.9, 8.1 Hz, 1H, ArH), 7.36–7.28 (m, 7H, ArH), 7.04 (ddd, J=1.2, 6.9, 8.1 Hz, 1H, ArH), 6.88 (s, 1H, NCH), 4.88 (t, J=7.5 Hz, 1H, ArCH), 3.76 (s, 3H, NCH$_3$), 3.22 (ddd, J=2.7, 8.4, 16.5 Hz, 1H, CH$_2$CO); 3.10 (ddd, J=2.7, 8.4, 16.5 Hz, 1H, CH$_2$CO); $^{13}$C NMR (75 MHz, CDCl$_3$) δ 201.8, 143.5, 137.3, 128.6, 127.6, 126.8, 126.6, 126.4, 121.9, 119.4, 119.0, 116.6, 109.3, 50.0, 37.4, 32.9; HRMS (CI) exact mass calcd for (C$_{15}$H$_{17}$NO) requires m/z 263.1310, found m/z 263.1306. [α]$_D$=+30.9 (CHCl$_3$). The enantiomeric ratio was determined by HPLC analysis of the alcohol, obtained by NaBH$_4$ reduction of the aldehyde, using a Chiracel AD and AD guard column (3:97 ethanol/hexanes, 1 mL/min); S isomer t$_r$=48.5 min and R isomer t$_r$=38.9 min.

EXAMPLE 17

(R)-4-Benzyloxy-3-(1-methyl-1H-indol-3-yl)-butanal (Table 2, entry 4): Prepared according to the general procedure from 4-benzyloxy-but-2-enal (286 mg, 1.50 mmol), 1-methyl-1H-indole (64 μL, 0.50 mmol), TFA (7.7 μL, 0.10 mmol) and (2S,5S)-5-benzyl-2-tert-butyl-3-methyl-imidazolidm-4-one (24.6 mg, 0.100 mmol) in CH$_2$Cl$_2$ (0.85 mL) and isopropanol (0.15 mL) at −83° C. for 18.5 h to provide, after silica gel chromatography (50:50 Et$_2$O/hexanes), the title compound as a colorless oil (134 mg, 84% yield, 96% ee). IR (film) 3056, 2957, 2894, 2830, 2722, 1717, 1618, 1600, 1582, 1550, 1478, 1451, 1370, 1331, 1309, 1272, 1223, 1173, 1110, 1070, 1024, 772, 740, 714 cm$^{-1}$; $^1$H NMR (300 MHz, CDCl$_3$) δ 9.77 (dd, J=2.1, 2.1 Hz, 1H, CHO), 8.04 (d, J=7.2 Hz, 2H, ArH), 7.75 (d, J=8.1 Hz, 1H, ArH), 7.61–724 (m, 5H, ArH), 7.17 (ddd, J=1.5, 6.6, 8.1 Hz, 1H, ArH), 6.96 (s, 1H, NCH), 4.73 (dd, J=5.1, 11.1 Hz, 1H, CH$_2$O). 4.42 (dd, J=8.7, 11.1 Hz, 1H, CH$_2$O), 4.12 (m, 1H, ArCH), 3.76 (s, 3H, NCH$_3$), 3.06 (ddd, J=2.1, 6.3, 16.8 Hz, 1H, CH$_2$CO); 2.96 (ddd, J=2.7, 8.4, 16.8 Hz, 1H, CH$_2$CO); $^{13}$C NMR (75 MHz, CDCl$_3$) δ 201.5, 166.4, 137.1, 133.1, 129.9, 129.6, 128.5, 126.8, 126.4, 122.1, 119.3, 119.0, 112.9, 109.6, 68.1, 46.5, 33.0, 31.2; HRMS (CI) exact mass calcd for (C$_{20}$H$_{19}$NO) requires m/z 321.1365, found m/z 321.1354. [α]$_D$=−2.0 (c=1.0, CHCl$_3$). The enantiomeric ratio was determined by HPLC analysis of the alcohol, obtained by NaBH$_4$ reduction of the aldehyde, using a Chiracel AS and AS guard column (4:96 ethanol/hexanes, 1 mL/min); S isomer t$_r$=42.9 min and R isomer t$_r$=53.2 min.

EXAMPLE 18

(R)-2-(1-Methyl-1H-indol-3-yl)-4-oxo butyric acid methyl ester (Table 2, entry 6): Prepared according to the general procedure from methyl 4-oxo-butenoate (171 mg, 1.50 mmol), 1-methyl-1H-indole (64 μL, 0.50 mmol), TFA (7.7 μL, 0.10 mmol) and (2S,5S)-5-benzyl-2-tert-butyl-3-methyl-imidazolidin-4-one (24.6 mg, 0.100 mmol) in CH$_2$Cl$_2$ (0.90 mL) and isopropanol (0.10 mL) at −85° C. for 21 h to provide, after silica gel chromatography (5:47:47 acetone/CH$_2$Cl$_2$/hexanes), the title compound as a colorless oil (109 mg, 89% yield, 91% ec). IR (film) 2937, 2833, 2729, 1732, 1623, 1545, 1477, 1436, 1379, 1332, 1228, 1171, 1042, 1016, 980, 773, 742 cm$^{-1}$; $^1$H NMR (300 MHz, CDCl$_3$) δ 9.81 (s, 1H, CHO), 7.67 (d, J=8.4 Hz, 1H, ArH), 7.33–7.23 (m, 2H, ArH), 7.15 (ddd, J=1.2, 7.6, 7.8 Hz, 1H, ArH), 6.98 (s, 1H, NCH), 4.44 (dd, J=5.4, 9.3 Hz, 1H, ArH), 3.76 (s, 3H, NCH$_3$), 3.69 (s, 3H, OCH$_3$), 3.47 (dd, J=9.3, 18.6 Hz, 1H, CH$_2$CO); 2.94 (dd, J=5.1, 18.3 Hz, 1H, CH$_2$CO); $^{13}$C NMR (75 MHz, CDCl$_3$) δ 200.1, 173.8, 137.0, 126.9, 126.5, 122.1, 119.5, 119.1, 110.8, 109.6, 52.5, 46.8, 36.5, 33.0; HRMS (CI) exact mass calcd for (C$_{14}$H$_{15}$NO$_3$) requires m/z 245.1048, found m/z 153.1151. [α]$_D$=−123.6 (c=1.0, CHCl$_3$). The enantiomeric ratio was determined by HPLC analysis of the alcohol, obtained by NaBH$_4$ reduction of the aldehyde, using a Chiracel AS and AS guard column (3:97 isopropanol/hexanes, 1 mL/min); S isomer t$_r$=71.7 min and R isomer t$_r$=76.3 min.

Examples 13–18, accordingly probe the scope of the α,β-unsaturated aldehyde substrate. The aldehyde reactants evaluated are given in Table 2, along with the reaction conditions and results of Examples 13–18:

TABLE 2

| entry | R | temp, °C. | time (h) | % yield | % ee[a] |
|---|---|---|---|---|---|
| 1 | CH$_3$ | −83 | 19 | 82 | 92[b] |
| 2 | n-propyl | −60 | 6 | 80 | 93 |
| 3 | i-propyl | −50 | 32 | 74 | 93 |
| 4 | CH$_2$—O-benzyl | −83 | 18 | 84 | 96[b] |
| 5 | phenyl | −55 | 45 | 84 | 90 |
| 6 | CO$_2$CH$_3$ | −83 | 21 | 89 | 91 |

TABLE 2-continued

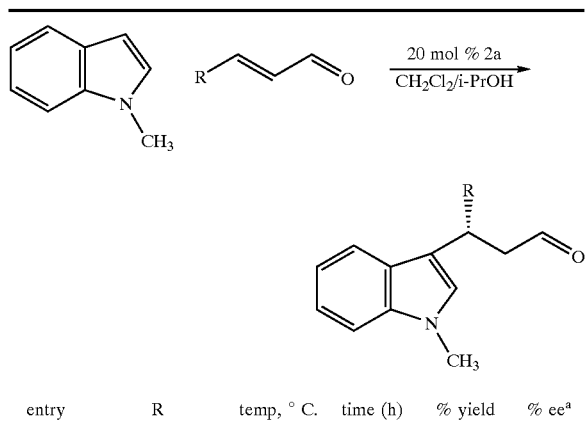

| entry | R | temp, °C | time (h) | % yield | % ee[a] |

[a]Product ratios determined by chiral HPLC.
[b]Absolute configuration determined by chemical correlation.

As may be seen in Table 2, the indole alkylation reaction is highly tolerant with to the steric contribution of the olefin substituent (R=CH$_3$, n-propyl, i-propyl, CH$_2$—O-benzyl, entries 1–4, ≧74% yield, ≧92% ee). As revealed in entries 5 and 6, the reaction can accommodate electron-deficient aldehydes that do not readily participate in iminium formation (R=CO$_2$CH$_3$, 91% ee) as well as stabilized iminium ions that might be less reactive towards Friedel-Crafts alkylation (R=phenyl, 90% ee). To demonstrate the preparative utility, the addition of 1-methyl-1H-indole to crotonaldehyde was performed on a 25 mmol scale with catalyst 2a to afford (R)-3 in 92% ee and 81% yield (entry 6).

EXAMPLE 19

(R)-3-(1H-Indol-3-yl)-butanal (Table 3, entry 2): Prepared according to general procedure from crotonaldehyde (100 μL, 1.25 mmol), indole (146 mg, 1.25 mmol), 2,4-dinitrobenzoic acid (53 mg, 0.25 mmol) and (2S,5S)-5-benzyl-2-tert-butyl-3-methyl-imidazolidin-4-one (62 mg, 0.25 mmol) in CH$_2$Cl$_2$ (2.25 mL) and isopropanol (0.25 mL) at −60° C. for 19 h at which time an additional 30 μL (0.36 mmol) of crotonaldehyde was added. The reaction was allowed to continue stirring for an additional 3 h to provide, after silica gel chromatography (20:80 EtOAc/hexanes), the title compound as a colorless oil (168 mg, 72% yield, 91% ee). IR (film) 3408, 2962, 2875, 2833, 2729, 1716, 1617, 1451, 1420, 1337, 1223, 1099, 1010, 772, 741 cm$^{-1}$; $^1$H NMR (300 MHz, CDCl$_3$) δ 9.77 (dd, J=2.1, 2.1 Hz, 1H, CHO), 8.15 (s, 1H, NH), 7.68 (dt, J=0.6, 7.8 Hz, 1H, ArH), 7.35 (dt, J=1.5, 7.8 Hz, 1H, ArH), 7.27–7.15 (m, 2H, ArH), 6.94 (d, J=2.4 Hz, 1H, NCH), 3.68 (dt, J=7.2, 21 Hz, 1H, ArCH), 2.91 (ddd, J=2.4, 6.9, 16.2 Hz, 1H, CH$_2$CO); 2.73 (ddd, J=2.1, 7.2, 16.2 Hz, 1H, CH$_2$CO); 1.47 (d, J=6.9 Hz, 3H, CHCH$_3$); $^{13}$C NMR (75 MHz, CDCl$_3$) δ 203.0, 136.5, 126.1, 122.1, 120.7, 120.1, 119.3, 118.9, 111.4, 50.9, 26.0, 21.6; HRMS (CI) exact mass calcd for (C$_{12}$H$_{13}$NO) requires m/z 187.0997, found m/z 153.0993. [α]$_D$=−2.2 (c=CHCl$_3$). The enantiomeric ratio was determined by HPLC analysis of the alcohol, obtained by NaBH$_4$ reduction of the aldehyde, using a Chiracel OD-H and OD guard column (10:90 ethanol/hexanes, 1 mL/min); S isomer t$_r$=20.2 min and R isomer t$_r$=17.6 min.

EXAMPLE 20

(R)-3-(1-Allyl-1H-indol-3-yl)-butanal (Table 3, entry 3): Prepared according to general procedure from crotonaldehyde (125 μL, 1.50 mmol), 1-allyl-1H-indole (78.5 mg, 0.500 mmol), TFA (7.7 μL, 0.10 mmol) and (2S,5S)-5-benzyl-2-tert-butyl-3-methyl-imidazolidin-4-one (24.6 mg, 0.100 mmol) in CH$_2$Cl$_2$ (0.90 mL) and isopropanol (0.10 mL) at −72° C. for 21 h to provide, after silica gel chromatography (7:93 EtOAc/hexanes), the title compound as a colorless oil (80 mg, 70% yield, 92% ee). IR (film) 3041, 2966, 2919, 2822, 2834, 2712, 1722, 1469, 1375, 1328, 1309, 1262, 192, 1018, 995, 929, 736 cm$^{-1}$; $^1$H NMR (300 MHz, CDCl$_3$) δ 9.76 (dd, J=2.1, 2.1 Hz, 1H, CHO), 7.64 (dt, J=0.9, 7.8 Hz, 1H, ArH), 7.33–7.20 (m, 2H, ArH), 7.13 (ddd, J=0.9, 6.9, 7.8 Hz, 1H, ArH), 6.89 (s, 1H, NCH), 5.98 (ddd, J=5.4, 9.9, 22.5 Hz, 1H, CH$_2$CHCH$_2$), 5.20 (dd, J=1.5, 10.2 Hz, 1H, CH$_2$CHCH$_2$), 5.10 (dt, J=1.5, 17.1 Hz, 1H CH$_2$CHCH$_2$), 4.68 (d, J=5.4 Hz, 2H NCH$_2$), 3.69 (dt, J=6.9, 21.3 Hz, 1H, ArCH), 2.88 (ddd, J=2.4, 6.6, 16.2 Hz, 1H, CH$_2$CO); 2.71 (ddd, J=2.1, 7.2, 16.2 Hz, 1H, CH$_2$CO); 1.44 (d, J=6.9 Hz, 3H, CHCH$_3$); $^{13}$C NMR (75 MHz, CDCl$_3$) δ 202.8, 136.7, 133.5, 126.8, 124.1, 121.8, 119.3, 119.2, 119.0, 117.4, 109.8, 51.1, 48.9, 26.1, 21.8; HRMS (CI) exact mass calcd for (C$_{15}$H$_{17}$NO) requires m/z 227.1310, found m/z 227.1309. [α]$_D$=−4.4 (c=1.0, CHCl$_3$). The enantiomeric ratio was determined by HPLC analysis of the alcohol, obtained by NaBH$_4$ reduction of the aldehyde, using a Chiracel AD and AD guard column (2:98 ethanol/hexanes, 1 mL/min); S isomer t$_r$=38.7 min and R isomer t$_r$=42.2 min.

EXAMPLE 21

(R)-3-(1-Benzyl-1H-indol-3-yl)-butanal (Table 3, entry 4): Prepared according to the general procedure from crotonaldehyde (125 μL, 1.50 mmol), 1-benzyl-1H-indole (104 mg, 0.500 mmol), 2,4-dinitrobenzoic acid (21.2 mg, 0.100 mmol) and (2S,5S)-5-benzyl-2-tert-butyl-3-methyl-imidazolidin-4-one (24.6 mg, 0.100 mmol) in CH$_2$Cl$_2$ (0.90 mL) and isopropanol (0.10 mL) at −60° C. for 41 h, at which time an additional 125 μL (1.50 mmol) of crotonaldehyde was added. The reaction was continued for an additional 70 h, at which time an additional 42 μL (0.50 mmol) of crotonaldehyde was added. The reaction was continued at this temperature for an additional 5 h, at which time the temperature was raised to −40° C. for 2 h, then −10° C. for an additional 2 h to provide, after silica gel chromatography (15:85 EtOAc/hexanes), the title compound as a colorless oil (110 mg, 80% yield, 89% ee). IR (film) 3062, 3030, 2965, 2925, 2877, 2820, 2724, 1722, 1613, 1589, 1549, 1496, 1480, 1468, 1452, 1392, 1372, 1356, 1331, 1303, 1251, 1203, 1174, 1017 cm$^{-1}$; $^1$H NMR (300 MHz, CDCl$_3$) δ 9.76 (dd, J=2.4, 2.4 Hz, 1H, CHO), 7.66 (dt, J=0.6, 7.5 Hz, 1H, ArH), 7.33–7.08 (m, 8H, ArH), 6.92 (s, 1H, NCH), 5.28 (s, 2H, NCH$_2$), 3.70 (dt, J=6.9, 21 Hz, 1H, ArCH), 2.89 (ddd, J=2.4, 6.6, 16.5 Hz, 1H, CH$_2$CO); 2.72 (ddd, J=1.8, 7.8, 15.9 Hz, 1H, CH$_2$CO); 1.44 (d, J=6.9 Hz, 3H, CHCH$_3$); $^{13}$C NMR (75 MHz, CDCl$_3$) δ 202.7, 137.5, 131.9, 128.8, 127.6, 126.9, 126.8, 124.6, 122.0, 119.6, 119.3, 119.2, 110.0, 51.2, 50.1, 26.1, 21.0; HRMS (CI) exact mass calcd for (C$_{19}$H$_{19}$NO) requires m/z 277.1467, found m/z 277.1464. [α]$_D$=+3.5 (c=1.0, CHCl$_3$). The enantiomeric ratio was determined by HPLC analysis of the alcohol, obtained by NaBH$_4$ reduction of the aldehyde, using a Chiracel AD and AD guard column (2:98 isopropanol/hexanes, 1 mL/min); S isomer t$_r$=26.5 min and R isomer t$_r$=29.5 min.

EXAMPLE 22

(R)-4-Benzyloxy-3-(4-methoxy-1-methyl-1H-indol-3-yl)-butanal (Table 3, entry 6): Prepared according to the general procedure from 4-benzyloxy-but-2-enal (285 mg, 1.50 mmol), 4-methoxy-1-methyl-1H-indole (80.5 mg, 0.500 mmol), TFA (7.7 µL, 0.10 mmol) and (2S,5S)-5-benzyl-2-tert-butyl-3-methyl-imidazolidin-4-one (24.6 mg, 0.100 mmol) in $CH_2Cl_2$ (0.90 mL) and isopropanol (0.10 mL) at −87° C. for 19.5 h to provide, after silica gel chromatography (20:80 EtOAc/hexanes), the title compound as a colorless oil (158 mg, 90% yield, 94% ee). IR (film) 3081, 2961, 2850, 2730, 1719, 1608, 1582, 1548, 1501, 1466, 1454, 1424, 1381, 1334, 1321, 1274,1261, 1180, 1116, 1073, 1026, 782, 714 cm$^{-1}$; $^1$H NMR (300 MHz, $CDCl_3$) δ 9.78 (dd, J=2.4, 2.4 Hz, 1H, CHO), 8.03–8.01 (m, 2H, ArH), 7.59–7.53 (m, 1H, ArH, 7.47–7.41 (m, 2H, ArH), 7.16 (t, J=8.4 Hz, 1H, ArH), 6.92 (dd, J=0.6, 8.4 Hz, 1H, ArH), 6.83 (s, 1H, NCH), 6.52 (d, J=7.5 Hz, 1H, ArH), 4.71 (dd, J=5.1, 10.5 Hz, 1H, $CH_2O$), 4.50 (dd, J=8.4, 10.5 Hz, 1H, $CH_2O$), 4.35 (m, 1H, ArCH), 3.94 (s, 1H, $OCH_3$), 3.71 (s, 3H, $NCH_3$), 2.98 (d, J=2.4 Hz, 1H, $CH_2CO$); 2.96 (d, J=2.7 Hz, 1H, $CH_2CO$); $^{13}$C NMR (75 MHz, $CDCl_3$) δ 202.5, 166.3, 154.2, 133.0, 130.3, 129.6, 128.6, 128.4, 125.4, 122.9, 116.8, 113.6, 102.8, 99.4, 68.8, 55.3, 47.3, 33.2, 32.2; HRMS (CI) exact mass calcd for ($C_{21}H_{21}NO_4$) requires m/z 351.1471, found m/z 351.1466. $[\alpha]_D$=−13.9 (c=1.0 $CHCl_3$). The enantiomeric ratio was determined by HPLC analysis of the alcohol, obtained by $NaBH_4$ reduction of the aldehyde, using a Chiracel AD and AD guard column (4:96 ethanol/hexanes, 1 mL/min); S isomer $t_r$=58.7 min and R isomer $t_r$=47.5 min.

EXAMPLE 23

(R)-4-Benzyloxy-3-(4-methyl-1H-indol-3-yl)-butanal (Table 3, entry 5): Prepared according to the general procedure from benzoic acid 4-benzyloxy-but-enal (143 mg, 0.750 mmol), 4-methyl-1H-indole (80.5 mg, 0.500 mmol), 2,4-dinitrobenzoic acid (21.2 mg, 0.100 mmol) and (2S,5S)-5-benzyl-2-tert-butyl-3-methyl-imidazolidin-4-one (24.6 mg, 0.100 mmol) in $CH_2Cl_2$ (0.90 mL) and isopropanol (0.10 mL) at −60° C. for 2.5 h to provide, after silica gel chromatography (15:85 EtOAc/hexanes), the title compound as a colorless oil (150 mg, 94% yield, 94% ee) after silica gel chromatography in 15% EtOAc/hexanes. IR (film) 3406, 2947, 2923, 2843, 2738, 1717, 1620, 1604, 1584, 1451, 1411, 1383, 1344, 1315, 1271, 1178, 1114, 1066, 1226, 969 cm$^{-1}$; $^1$H NMR (300 MHz, $CDCl_3$) δ 9.82 (dd, J=2.1, 2.1 Hz, 1H, CHO), 8.14 (s, 1H, NH), 8.02 (dt, J=1.5, 7.2 Hz, 2H, ArH), 7.58 (tt, J=1.5, 6.6 Hz, 1H, ArH), 7.45 (tt, J=1.2, 6.9 Hz, 2H, ArH), 7.24–7.08 (m, 3H, ArH, NCH), 6.91 (dt, J=0.9, 7.2 Hz, 1H, ArH), 4.74 (dd, J=4.2, 10.5 Hz, 1H, $CH_2O$), 4.52–4.43 (m, 1H, ArCH), 4.32 (dd, J=8.4, 10.8 Hz, 1H, $CH_2O$), 3.05 (ddd, J=2.1, 6.9, 16.8 Hz, 1H, $CH_2CO$); 2.95 (ddd, J=2.1, 7.8, 16.8 Hz, 1H, $CH_2CO$), 2.82 (s, 3H, $ArCH_3$); $^{13}$C NMR (75 MHz, $CDCl_3$) δ 201.3, 166.3,136.5, 133.2, 130.5, 130.0, 129.7, 128.5, 125.1, 122.6, 122.1, 121.7, 115.8, 109.4, 68.9, 47.8, 31.7, 21.0; HRMS (CI) exact mass calcd for ($C_{20}H_{19}NO_3$) requires m/z 321.1365, found m/z 321.1353. $[\alpha]_D$=−26.6 (c=1.0, $CHCl_3$). The enantiomeric ratio was determined by HPLC analysis of the alcohol, obtained by $NaBH_4$ reduction of the aldehyde, using a Chiracel AD and AD guard column (10:90 ethanol/hexanes, 1 mL/min); S isomer $t_r$=47.8 min and R isomer $t_r$=42.4 min.

EXAMPLE 24

(R)-4-Benzyloxy-3-(6-chloro-1H-indol-3-yl)-butanal (Table 3, entry 7): Prepared according to the general procedure from 4-benzyloxy-but-2-enal (143 mg, 0.750 mmol), 6-chloro-1H-indole (75.8, 0.500 mmol), 2,4-dinitrobenzoic acid (21.2 mg, 0.100 mmol) and (2S,5S)-5-benzyl-2-tert-butyl-3-methyl-imidazolidin-4-one (24.6 mg, 0.100 mmol) in $CH_2Cl_2$ (0.90 mL) and isopropanol (0.10 mL) at −60° C. for 12.75 h to provide, after silica gel chromatography ($CH_2Cl_2$), the title compound as a colorless oil (124 mg, 73% yield, 97% ee) after silica gel chromatography in $CH_2Cl_2$. IR (film) 3383, 2953, 2930, 2834, 2734, 1718, 1623, 1603, 1548, 1453, 1403, 1378, 1273, 1184, 1104, 1069, 1019, 909, 804, 774, 714 cm$^{-1}$; $^1$HNMR (300 MHz, $CDCl_3$) δ 9.77 (dd, J=1.8, 1.8 Hz, 1H, CHO), 8.15 (s, 1H, NH), 8.02–7.99 (m, 2H, ArH), 7.65 (dd, J=0.6, 8.7 Hz, 1H, ArH), 7.58 (tt, J=1.5, 6.6 Hz, 1H, ArH), 7.48–7.42 (m, 2H, ArH), 7.37 (d, J=1.8 Hz, 1H NCH), 7.12 (dt, J=2.1, 8.7 Hz, 2H, ArH), 4.70 (dd, J=5.1, 10.8 Hz, 1H, $CH_2O$), 4.42 (dd, J=8.4, 11.1 Hz, 1H, $CH_2O$), 4.08 (m, 1H, ArCH), 3.06 (ddd, J=1.8, 6.3. 16.8 Hz, 1H, $CH_2CO$); 2.95 (ddd, J=2.1, 7.8, 16.5 Hz, 1H, $CH_2CO$); $^{13}$C NMR (75 MHz, $CDCl_3$) δ 200.9, 166.5, 136.7, 135.4, 133.2, 129.9, 129.6, 128.5. 125.1, 122.3, 120.7, 119.8, 115.0, 111.4, 67.8, 46.5, 31.0; HRMS (CI) exact mass calcd for ($C_{19}H_{16}ClNO_3$) requires m/z 341.0819, found m/z 341.0814.$[\alpha]_D$=−3.3 (c=1.0 $CHCl_3$). The enantiomeric ratio was determined by HPLC analysis of the alcohol, obtained by $NaBH_4$ reduction of the aldehyde, using a Chiracel AD and AD guard column (10:90 ethanol/hexanes, 1 mL/min); S isomer $t_r$=38.8 min and R isomer $t_r$=43.3 min.

Examples 19–24, summarized in Table 3, thus demonstrate that conjugate addition catalyzed by an imidazolidinone salt of the invention is also general with respect to indole architecture:

TABLE 3

| entry | R | Y | Z | temp, ° C. | time (h) | % yield | % ee[a] |
|---|---|---|---|---|---|---|---|
| 1 | $CH_3$ | H | H | −87 | 19 | 82 | 92[b] |
| 2 | H | H | H | −60 | 22 | 72 | 91[b] |
| 3 | allyl | H | H | −72 | 20 | 70 | 92 |
| 4 | benzyl | H | H | −60 | 120 | 80 | 89[b] |
| 5 | H | H | $CH_3$ | −60 | 3 | 94 | 94[c] |
| 6 | $CH_3$ | H | $OCH_3$ | −87 | 19 | 90 | 96[c] |
| 7 | H | Cl | H | −60 | 13 | 73 | 97[c] |

[a]Product ratios determined by chiral HPLC.
[b]Absolute configuration determined by chemical correlation.
[c]Reaction conducted with (E)-BzOCH$_2$CH═CHCHO.

As indicated in Table 3, variation in the N-substituent (X=H, $CH_3$, benzyl, allyl, 1–4) is possible without significant loss in yield or enantioselectivity (≧70% yield, 89–92% ee). The results obtained upon incorporation of alkyl and alkoxy substituents at the C(4)-indole position reveals that electronic and steric modification of the indole ring can be accomplished with little influence on reaction selectivity (entries 5 and 6, ≧90% yield, 94–96% ee ). As revealed in entry 7, electron deficient nucleophiles have been successfully utilized in the context of a 6-chloro substituted indole (73% yield, 97% ee). Such halogenated indole adducts can serve as valuable synthons for use in conjunction with established organometallic technologies, e.g., Buchwald-Hartwig couplings (Wolfe et al. (1999) *Angew. Chem.-Int. Edit. Engl.* 38:2413–2416; Hartwig (1998) *Accounts Chem. Res.* 31:852) and Stille couplings (Stille (1986) *Angew. Chem.-Int. Edit. Engl.* 25:508).

Examples 25 and 26 provide a demonstration of the utility of this organocatalytic indole alkylation reaction in providing rapid enantioselective access to biologically relevant molecules. Example 26 describes synthesis of the indolobutyric acid (4), a COX-2 inhibitor Black et al. (1996) *Bioorg. Med. Chem. Lett.* 6:725, via organocatalytic alkylation of the 5-methoxy-2-methylindole (3) (synthesized in Example 25) with (E)-crotonaldehyde, followed by oxidation of the formyl moiety:

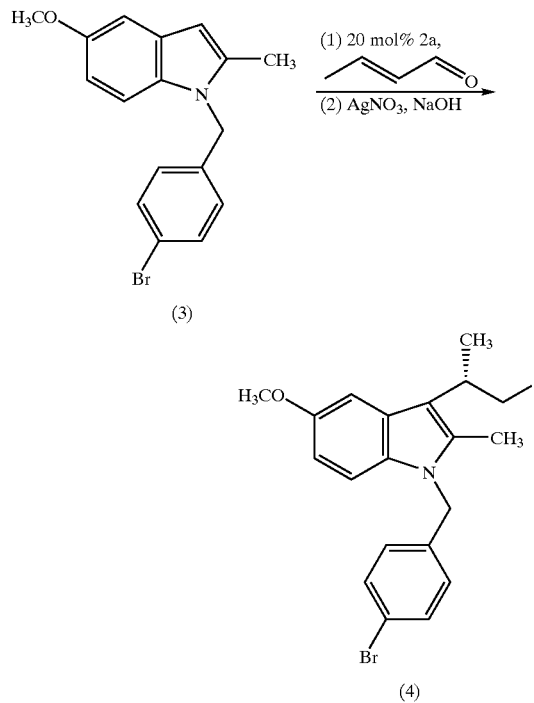

EXAMPLE 25

(R)-3-[1-(4-Bromo-benzyl)-5-methoxy-2-methyl-1H-indol-3-yl]-butanal (3): To 1-(4-bromo-benzyl)-5-methoxy-2-methyl-1H-indole (110 mg, 0.333 mmol) in a 2-dram amber vial was added $CH_2Cl_2$ (0.60 mL), isopropanol (0.066 mL), dichloroacetic acid (5.5 μL, 0.066 mmol) and (2S,5S)-5-benzyl-2-tert-butyl-3-methyl-imidazolidin-4-one (16.4 mg, 0.066 mmol). This solution was stirred for 10 min at room temperature, then placed in a −70° C. bath for an additional 10 min. At this time, crotonaldehyde (82 μL, 1.0 mmol) was added and the reaction was stirred at −70° C. for 9 h. The reaction mixture was then transferred cold through a silica plug into a flask and concentrated to provide, after silica gel chromatography (20:80 EtOAc/hexanes), the title compound as a colorless oil (111 mg, 84% yield, 87% ee). IR (film) 2930, 2823, 2730, 1722, 1618, 1581, 1530, 1483, 1452, 1405, 1229, 1156, 1073, 1037, 1011, 902, 798, 476 $cm^{-1}$; $^1H$ NMR (300 MHz, $CDCl_3$) δ 9.69 (dd, J=1.8, 1.8 Hz, 1H, CHO), 7.38 (dt, J=2.4, 9.0 Hz, 2H, ArH), 7.12 (d, J=2.1 Hz, 1H, ArH), 7.05 (d, J=9.0, 1H, ArH), 6.79–6.75 (m, 3H, ArH), 5.19 (s, 2H $NCH_2$), 3.88 (s, 3H, $OCH_3$), 3.66 (dt, J=7.2, 22.2 Hz, 1H ArCH), 3.02 (ddd, J=1.8, 8.1, 16.5 Hz, 1H, $CH_2CO$); 2.85 (ddd, J=2.1, 6.6, 16.5 Hz, 1H, $CH_2CO$); 2.30 (s, 3H, $ArCH_3$) 1.48 (d, J=7.2 Hz, 3H, $CHCH_3$); $^{13}C$ NMR (75 MHz, $CDCl_3$) δ 202.5, 153.6, 137.0, 132.7, 132.0, 131.9, 127.6, 126.6, 121.1, 114.5, 110.0, 109.8, 102.3, 56.2, 50.6, 46.2, 26.4, 21.4, 10.9; HRMS (CI) exact mass calcd for ($C_{21}H_{22}BrNO_2$) requires m/z 399.0834, found m/z 399.0833. $[α]_D$=−20.8 (c=1.0, $CHCl_3$). The enantiomeric ratio was determined by HPLC analysis of the alcohol, obtained by $NaBH_4$ reduction of the aldehyde, using a Chiracel OD-H and OD guard column (4:96 ethanol/hexanes, 1 mL/min); S isomer $t_r$=45.1 min and R isomer $t_r$=35.9 min.

EXAMPLE 26

(R)-3-[1-(4-Bromo-benzyl)-5-methoxy-2-methyl-1H-indol-3-yl]-butyric acid (4): A solution of (R)-3-[1-(4-Bromo-benzyl)-5-methoxy-2-methyl-1H-indol-3-yl]-butanal (110 mg, 0.250 mmol) and silver nitrate (59.7 mg, 0.275 mmol) in 1.3 ml absolute ethanol was treated with a solution of 5N NaOH in ethanol (1:5, 0.9 ml, 0.75 mmol NaOH). After 45 min this was treated with 10 ml water, acidified to pH 3 and extracted with $CHCl_3$ (5×20 ml) rinsing each extract with brine. The combined organics were dried over $Na_2SO_4$ and concentrated in vacuo to provide, after silica gel chromatography the title compound as a pale yellow solid (101 mg, 97% yield). IR (film) 3425, 2961, 2934, 2833, 1706, 1483, 1451, 1405, 1228, 1156, 1010, 796, 755 $cm^{-1}$; $^1H$ NMR (300 MHz, $CDCl_3$) δ 7.36 (d, J=9.0 Hz, 2H, ArH), 7.11 (d, J=2.4 Hz, 1H, ArH), 7.04 (d, J=8.7, 1H, ArH), 6.77–6.73 (m, 3H, ArH), 5.18 (s, 2H $NCH_2$), 3.86 (s, 3H, $OCH_3$) 3.56 (dt, J=7.2, 21.9 Hz, 1H ArCH), 2.86 (d, J=3.6 Hz, 1H, $CH_2CO$); 2.83 (d, J=3.3 Hz, 1H, $CH_2CO$); 2.27 (s, 3H, $ArCH_3$) 1.49 (d, J=7.2 Hz, 3H, $CHCH_3$); $^{13}C$ NMR (75 MHz, $CDCl_3$) δ 178.0, 153.7, 137.3, 133.8, 133.0, 132.0, 127.7, 126.7, 121.2, 118.8, 114.6, 110.1, 109.9, 102.4, 56.3, 46.3, 41.5, 28.6, 21.1, 10.9; HRMS (CI) exact mass calcd for ($C_{21}H_{23}BrNO_3$) (M+1) requires m/z 416.0861, found m/z 416.0867. $[α]_D$=−30.9 (c=1.0, $CHCl_3$).

EXAMPLE 27

Determination of Absolute Stereochemistry (a) Determination of the absolute stereochemistry of (R)-3-(1H-indol-3-yl)-butanal by correlation to (S)-3-(1H-indol-3-yl)-butyric acid methyl ester, using the method of Takeda et al. (1980) *Chem. Lett.*, p. 163, as follows:

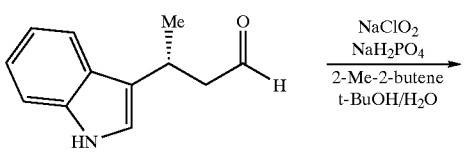

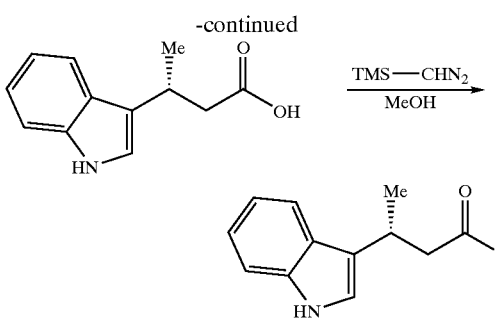

3-(1H-Indol-3-yl)-butanal (130 mg, 0.690 mmol) was dissolved in tert-butyl alcohol (27 mL) and 2-methyl-2-butene (4.7 mL) and subsequently was stirred for 10 min. To this solution was added an aqueous solution (4.7 mL) of NaClO$_2$ (75 mg, 0.83 mmol) and NaH$_2$PO$_4$ (115 mg, 0.830 mmol) in one portion. The reaction mixture was stirred at room temperature for 12 h. The organics were removed by concentrating in vacuo. The residue was diluted with 10 mL of H$_2$O, and adjusted to a neutral pH with 1M HCl. Extraction with EtOAc (3×10 mL), drying over Na$_2$SO$_4$, and concentration in vacuo provided 3-(1H-indol-3-yl)-butanoic acid. TMS-diazomethane was added dropwise to a solution of the crude 3-(1H-indol-3-yl)-butanoic acid in methanol (7 mL) until a yellow color persisted. The residual TMS-diazomethane was quenched by the dropwise addition of acetic acid until the yellow color disappeared. The reaction was then treated with an excess of saturated aqueous sodium bicarbonate, extracted with Et$_2$O (3×20 ml), dried over Na$_2$SO$_4$ and purified by silica gel chromatography (20:80 EtOAc/hexanes to provide (R)-3-(1H-indol-3-yl)-butyric acid methyl ester. $[\alpha]_D = -7.6$ (c=1.0 benzene); reported rotation for (S)-3-(1H-indol-3-yl)-butyric acid methyl ester $[\alpha]_D = +10.9$ (c=2.12, benzene).

(b) Determination of the absolute stereochemistry of (R)-3-(1-benzyl-1H-indol-3-yl)-butanal by correlation to (R)-3-(1H-indol-3-yl)-butanal:

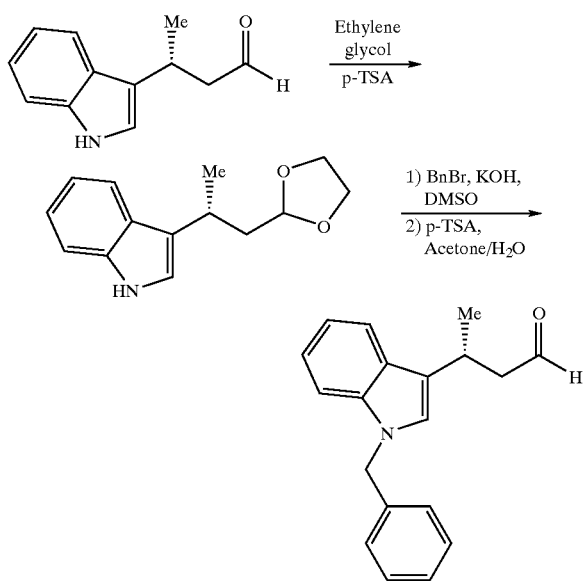

(R)-3-(1H-Indol-3-yl)-butanal (89.5 mg, 0.479 mmol) was treated with ethylene glycol (130 μL, 2.4 mmol) and a catalytic amount of p-TSA in CH$_2$Cl$_2$ (2 mL). The reaction was stirred at room temperature for 12 h, at which time the organics were removed in vacuo. The solution was diluted with H$_2$O (10 mL) and extracted with Et$_2$O (3×20 mL). The collected organics where washed with brine, dried over Na$_2$SO$_4$ and concentrated in vacuo to provide (R)-3-(2-[1,3]-dioxolan-2-yl-1-methyl-ethyl)-1H-indole (15.7 mg 0.0680 mmol) after silica gel chromatography (20:80 EtOAc/hexanes). This residual material was then exposed to 1 mL of DMSO, finely crushed KOH (15.3 mg, 0.272 mmol), and benzyl bromide (12 μL, 0.13 mmol) at 0° C., then the solution was allowed to warm to room temperature and stirred for 12 h. The reaction was then treated with water (10 ml), and extracted with Et$_2$O (2×20 ml). The aqueous layer was acidified to pH 4, extracted with Et$_2$O 3×20 ml), dried over Na$_2$SO$_4$ and concentrated in vacuo to provide 14.7 mg of (R)-1-benzyl-3-(2-[1,3]dioxolan-2-yl-1-methyl)-1H-indole after preparative TLC (20:80 EtOAc/hexanes). The benzylated product was then refluxed with a catalytic amount of p-TSA in H$_2$O (1 mL)/acetone (2 mL) overnight. The reaction mixture was diluted with H$_2$O (5 mL), and extracted with Et$_2$O (3×10 mL). The collected organics were washed with brine, dried over Na$_2$SO$_4$ and concentrated in vacuo to provide (R)-3-(1-benzyl-1H-indol-3-yl)-butanal (5.5 mg, 0.020 mmol) after preparative TLC. $[\alpha]_D = +3.8$ (c=1.0, CHCl$_3$); reported rotation for (R)-3-(1-benzyl-1H-indol-3-yl)-butanal $[\alpha]_D = +3.5$ (c=1.0, CHCl$_3$).

(c) Determination of the absolute stereochemistry of (R)-3-(1-methyl-1H-indol-3-yl)-butanal by correlation to (R)-3-(1H-indol-3-yl)-butanal:

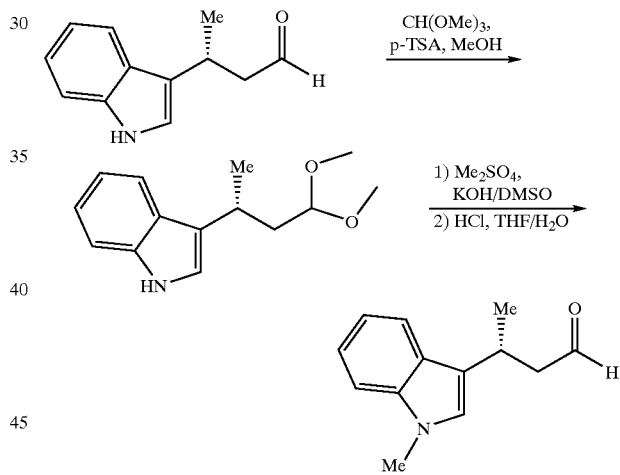

(R)-3-(1H-Indol-3-yl)-butanal (236 mg, 1.26 mmol) was dissolved in methanol (15 mL) and treated with trimethyl orthoformate (275 μl, 2.50 mmol) and a catalytic amount of p-TSA. The reaction was stirred at room temperature for 3 hours, at which time H$_2$O (10 mL) was added and the reaction was extracted with ether (3×20 mL). The collected organics were rinsed with brine, dried over Na$_2$SO$_4$, and concentrated in vacuo to provide 3-(3,3-dimethoxy-1-methyl-propyl)-1H-indole (228 mg, 1.17 mmol). 3-(3,3-dimethoxy-1-methyl-propyl)-1H-indole (39.9 mg, 0.171 mmol) was dissolved in a KOH (38.4 mg, 0.684 mmol)/DMSO (2 mL) solution and allowed to stir at 0° C. for 10 min, at which time dimethyl sulfate (32.5 μl, 0.340 mmol) was added and the reaction was allowed to warm to room temperature. The reaction was left to stir at room temperature until it appeared done by TLC. The reaction was quenched with H$_2$O (1 mL) and brought to a neutral pH with dropwise addition of 1M HCl. The solution was extracted with Et$_2$O (3×5 mL), and the collected organics were rinsed with brine, dried over Na$_2$SO$_4$, and concentrated in vacuo to provide 3-(3,3-dimethoxy-1-methyl-propyl)-1-methyl-indole. This crude residual material was dissolved in THF (5 mL) and 1M HCl (1 mL) to give (R)-3-(1-methyl-1H-indol-3-yl)-butanal (1.9 mg, 0.0094 mmol) after preparative TLC (25:75 EtOAc/hexanes). [α]$_D$=−4.1 (c=1.0, CHCl$_3$); reported rotation for (R)-3-(1-methyl-1H-indol-3-yl)-butanal [α]$_D$=−4.2 (c=1.0, CHCl$_3$).

(d) Determination of the absolute stereochemistry (R)-4-benzyloxy-3-(1-methyl-1H-indol-3-yl)-butanal by correlation to (R)-3-(1H-indol-3-yl)-butanal:

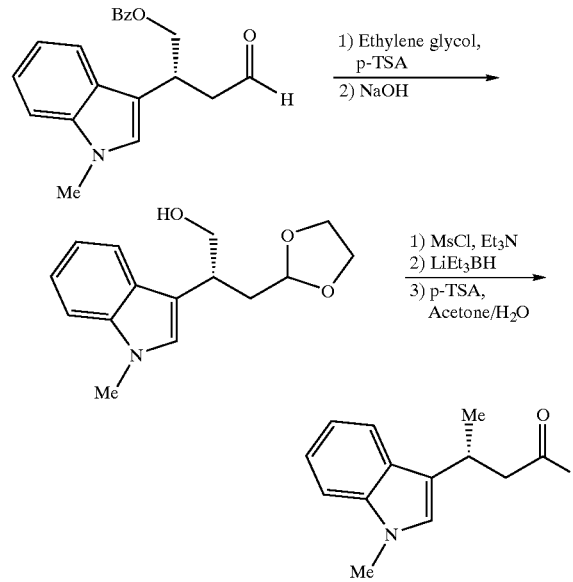

(R)-Benzoic acid 2-(1-methyl-1H-indol-3-yl)-4-oxo-butyl ester (1.65 g, 5.10 mmol) was dissolved in CH$_2$Cl$_2$ (50 mL). This solution was treated with p-TSA (20 mg) and ethylene glycol (1.4 mL, 26 mmol). The reaction was stirred at room temperature overnight, at which time the organics were removed in vacuo. The solution was diluted with H$_2$O (10 mL) and extracted with Et$_2$O (3×20 mL). The collected organics were washed with brine, dried over Na$_2$SO$_4$ and concentrated in vacuo to provide (R)-benzoic acid 3-[1,3]dioxolan-2-yl-2-(1-methyl-1H-indol-3-yl)-propyl ester. The unpurified product was dissolved in MeOH/THF (18 mL/18 mL) and allowed to stir at room temperature for 10 min. To this was added a 4% NaOH/MeOH (18 mL) solution. The reaction was allowed to stir at room temperature for 1 h. The solution was diluted with H$_2$O (10 mL) and extracted with Et$_2$O (3×20 mL). The collected organics were washed with brine, dried over Na$_2$SO$_4$ and concentrated in vacuo to provide (R)-3-[1,3]dioxolan-2-yl-2-(1-methyl-1H-indol-3-yl)-propan-1-ol (600 mg, 2.30 mmol) after silica gel chromatography (50:50 Et$_2$O/hexanes). 50% Et$_2$O/hexanes). (R)-3-[1,3]Dioxolan-2-yl-2-(1-methyl-1H-indol-3-yl)-propan-1-ol (69.5 mg, 0.267 mmol) was dissolved in CH$_2$Cl$_2$ (8 mL) and Et$_3$N (56 μl, 0.40 mmol). The reaction was cooled to 0° C. and treated with methanesulfonyl chloride (31 μl, 0.40 mmol). The reaction stirred for 1.5 h at this temperature then was allowed to warm to room temperature and stirred for an additional 10 min. The solution was diluted with H$_2$O (5 mL) and extracted with Et$_2$O (3×10 mL). The collected organics were washed with brine, dried over Na$_2$SO$_4$ and concentrated in vacuo to provide (R)-methanesulfonic acid 3-[1,3]dioxolan-2-yl-2-(1-methyl-1H-indol-3-yl)-propyl ester. Deoxygenation was performed following the method of Holder and Matturro (1977) *J. Org. Chem.* 42:2166.

The unpurified material was dissolved in THF (2.7 mL) and the system was purged with an inert nitrogen atmosphere. Lithium triethylborohydride (560 μl, 1M solution in THF) was added in one portion and the reaction was allowed to reflux for 1 h under an nitrogen. The system was allowed to come to room temperature and was then cooled to 0° C. via an ice bath. Excess hydride was quenched by the dropwise addition of H$_2$O. Organoboranes were oxidized by adding 190 μl of a 3N NaOH solution followed by slow dropwise addition of 115 μl of 50% H$_2$O$_2$. The ice bath was removed and the reaction mixture was allowed to reflux for an additional hour. After cooling to room temperature, the mixture was diluted with 2.7 mL H$_2$O and extracted with pentane. The collected pentane layers were washed with H$_2$O, dried with MgSO$_4$, and concentrated in vacuo to provide (R)-3-(2-[1,3]dioxolan-2-yl-1-methyl-ethyl)-1-methyl-1H-indole. The unpurified material was dissolved in 8 ml acetone and 2 ml H$_2$O, treated with PPTS and warmed to reflux for 24 h. The reaction was diluted with H$_2$O (5 mL) and extracted with Et$_2$O (3×10 mL). The collected organics were washed with brine, dried over Na$_2$SO$_4$ and concentrated in vacuo to provide (R)-3-(1-methyl-1H-indol-3-yl)-butanal after preparative TLC (benzene). [α]$_D$=−4.6 (c=1.0, CHCl$_3$); reported rotation for (R)-3-(1-methyl-1H-indol-3-yl)-butanal [α]$_D$=−4.2 (c=1.0, CHCl$_3$).

I claim:

1. A process for catalyzing a reaction between an α,β-unsaturated aldehyde and a second reactant by lowering the energy level of the lowest unoccupied molecular orbital (LUMO) of the aldehyde, comprising:

contacting an α,β-unsaturated aldehyde with the second reactant in the presence of a catalyst comprised of an acid addition salt of compound (IIA) or (IIB) and a Bronsted acid

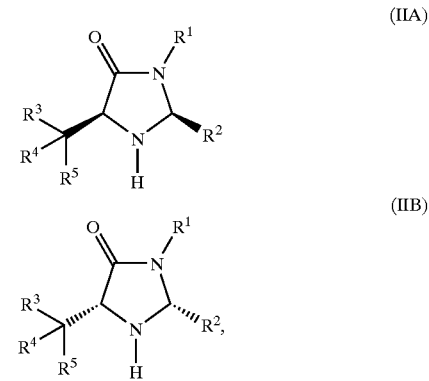

wherein:

R$^1$ is selected from the group consisting of C$_1$–C$_{12}$ hydrocarbyl, substituted C$_1$–C$_{12}$ hydrocarbyl, heteroatom-containing C$_1$–C$_{12}$ hydrocarbyl, and substituted heteroatom-containing C$_1$–C$_{12}$ hydrocarbyl;

R$^2$ has the structure —(L)$_m$—CR$^6$R$^7$R$^8$ wherein m is zero or 1, L is C$_1$–C$_6$ alkylene, and R$^6$, R$^7$ and R$^8$ are C$_1$–C$_{12}$ hydrocarbyl;

R$^3$ and R$^4$ are independently selected from the group consisting of hydrogen, halo, hydroxyl, C$_1$–C$_{12}$ hydrocarbyl, substituted C$_1$–C$_{12}$ hydrocarbyl, heteroatom-containing C$_1$–C$_{12}$ hydrocarbyl, and substituted heteroatom-containing C$_1$–C$_{12}$ hydrocarbyl; and $R^5$ is a cyclic group optionally substituted with 1 to 4 non-hydrogen substituents and containing zero to 3 heteroatoms, wherein the second reactant is capable of reacting with the aldehyde by virtue of the lowered LUMO of the aldehyde in the presence of the catalyst.

2. The process of claim 1, wherein the α,β-unsaturated aldehyde has the structure of formula (III)

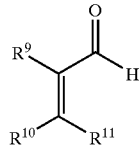

(III)

in which $R^9$, $R^{10}$ and $R^{11}$ are independently selected from the group consisting of hydrogen, $C_1$–$C_{30}$ hydrocarbyl, heteroatom-containing $C_1$–$C_{30}$ hydrocarbyl, substituted $C_1$–$C_{30}$ hydrocarbyl, substituted heteroatom-containing $C_1$–$C_{30}$ hydrocarbyl, and functional groups.

3. The process of claim 2, wherein $R^9$, $R^{10}$ and $R^{11}$ are independently selected from the group consisting of hydrogen, $C_1$–$C_{24}$ alkyl, $C_2$–$C_{24}$ alkenyl, $C_2$–$C_{24}$ alkynyl, $C_1$–$C_{24}$ alkoxy, $C_2$–$C_{24}$ alkenyloxy, $C_2$–$C_{24}$ alkynyloxy, $C_5$–$C_{30}$ aryl, $C_5$–$C_{30}$ aryloxy, $C_2$–$C_{24}$ alkoxyalkyl, $C_6$–$C_{30}$ aryloxyalkyl, hydroxyl, sulfhydryl, $C_2$–$C_{24}$ alkylcarbonyl, $C_6$–$C_{30}$ arylcarbonyl, $C_2$–$C_{24}$ alkoxycarbonyl, $C_6$–$C_{30}$ aryloxycarbonyl, halocarbonyl, $C_2$–$C_{24}$ alkylcarbonato, $C_6$–$C_{30}$ arylcarbonato, carboxy, carboxylato, carbamoyl, mono- and di-($C_1$–$C_{24}$ alkyl)-substituted carbamoyl, mono- and di-($C_5$–$C_{20}$ aryl)-substituted carbamoyl, amino, mono- and di-($C_1$–$C_{24}$ alkyl)-substituted amino, mono- and di-($C_5$–$C_{20}$ aryl)-substituted amino, $C_2$–$C_{24}$ alkylamido, $C_6$–$C_{30}$ arylamido, imino, $C_2$–$C_{24}$ alkylimino, $C_6$–$C_{30}$ arylimino, nitro, nitroso, sulfo, sulfonato, $C_1$–$C_{24}$ alkylsulfanyl, $C_5$–$C_{30}$ arylsulfanyl, $C_1$–$C_{24}$ alkylsulfinyl, $C_5$–$C_{30}$ arylsulfinyl, $C_1$–$C_{24}$ alkylsulfonyl, $C_5$–$C_{30}$ arylsulfonyl, phosphono, phosphonato, phosphinato, phospho, phosphino, and combinations thereof, and further wherein any two of $R^9$, $R^{10}$ and $R^{11}$ taken together can form a cyclic structure selected from five-membered rings, six-membered rings, and fused five-membered and/or six-membered rings, wherein the cyclic structure is aromatic, alicyclic, heteroaromatic, or heteroalicyclic, and has zero to 4 non-hydrogen substituents and zero to 3 heteroatoms.

4. The process of claim 3, wherein $R^9$ and $R^{11}$ are hydrogen.

5. The process of claim 4, wherein $R^{10}$ is selected from the group consisting of hydrogen, $C_1$–$C_{12}$ alkyl, $C_1$–$C_{12}$ alkoxy, $C_5$–$C_{20}$ aryl, $C_2$–$C_{12}$ alkoxyalkyl, and $C_6$–$C_{20}$ aryloxyalkyl.

6. The process of claim 5, wherein $R^{10}$ is selected from the group consisting of hydrogen, $C_1$–$C_6$ alkyl, $C_5$–$C_{12}$ aryl, and $C_6$–$C_{12}$ aryloxyalkyl.

7. The process of claim 2, wherein the second reactant is directly or indirectly bound to the aldehyde, such that the reaction is intramolecular.

8. The process of claim 7, wherein the second reactant is a 1,3-diene substituent, and the intramolecular reaction is a Diels-Alder reaction.

9. The process of claim 2, wherein the reaction is selected from the group consisting of cycloaddition reactions, 1,4 nucleophilic conjugate addition reactions, 1,4 radical addition reactions, organometallic insertions reactions, ene reactions, and any combination thereof occurring in tandem.

10. The process of claim 9, wherein the reaction is a cycloaddition reaction.

11. The process of claim 10, wherein the cycloaddition reaction is a [2+2] cycloaddition reaction, a [3+2] cycloaddition reaction, or a [4+2] cycloaddition reaction.

12. The process of claim 11, wherein the cycloaddition reaction is a [4+2] cycloaddition reaction.

13. The process of claim 12, wherein the second reactant is a 1,3-diene and the [4+2] cycloaddition reaction is a Diels-Alder reaction.

14. The process of claim 9, wherein the reaction is a 1,4 nucleophilic conjugate addition reaction.

15. The process of claim 14, wherein the 1,4 nucleophilic conjugate addition reaction comprises 1,4 carbon addition, 1,4 amine addition, 1,4 oxygen addition, 1,4 sulfur addition, 1,4 hydride addition or 1,4 organometallic addition.

16. The process of claim 14, wherein the second reactant is a nucleophile containing a pi bond, a lone pair-bearing heteroatom, or a negative charge.

17. The process of claim 16, wherein the second reactant is an aromatic or heteroaromatic compound, and the reaction is an alkylation reaction.

18. The process of claim 17, wherein the second reactant is an aromatic compound comprised of two or more fused aromatic rings.

19. The process of claim 18, wherein at least one of the aromatic rings is an N-heterocycle.

20. The process of claim 19, wherein the second reactant has the structure of formula (IV)

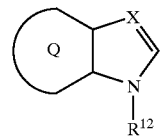

(IV)

wherein:

$R^{12}$ is selected from the group consisting of hydrogen, hydrocarbyl, substituted hydrocarbyl, heteroatom-containing hydrocarbyl, and substituted heteroatom-containing hydrocarbyl;

Q is a five- or six-membered aromatic ring containing zero to 3 heteroatoms selected from N, O and S and zero to 4 nonhydrogen substituents, wherein any two adjacent nonhydrogen substituents may together form an additional aryl, substituted aryl, heteroaryl, or heteroaryl substituent; and X is N or $CR^{13}$ wherein $R^{13}$ is hydrogen, hydrocarbyl, substituted hydrocarbyl, heteroatom-containing hydrocarbyl, or substituted heteroatom-containing hydrocarbyl.

21. The process of claim 20, wherein:

Q is phenyl substituted with zero to 2 nonhydrogen substituents selected from the group consisting of $C_1$–$C_{12}$ alkyl, $C_1$–$C_{12}$ alkoxy, and halo;

$R^{12}$ is selected from the group consisting of hydrogen, $C_1$–$C_{12}$ alkyl, $C_1$–$C_{12}$ alkenyl, $C_5$–$C_{20}$ aryl, and $C_5$–$C_{20}$ aralkyl; and X is $CR^{13}$.

22. The process of claim 21, wherein $R^{13}$ is H.

23. The process of claim 21, wherein $R^{13}$ is hydrocarbyl, substituted hydrocarbyl, heteroatom-containing hydrocarbyl, or substituted heteroatom-containing hydrocarbyl.

24. The process of claim 23, wherein $R^{13}$ is —$L^1$—Nu: wherein $L^1$ is a hydrocarbylene, substituted hydrocarbylene, heteroatom-containing hydrocarbylene, or substituted heteroatom-containing hydrocarbylene linker with 2 to 6 atoms in the linker backbone, and Nu: is a nucleophilic group capable of addition to an unsaturated bond.

25. The process of claim 24, wherein $L^1$ is substituted or unsubstituted $C_2$–$C_6$ alkylene.

26. The process of claim 25, wherein $L^1$ is $C_2$–$C_4$ alkylene.

27. The process of claim 26, wherein $L^1$ is ethylene.

28. The process of claim 24, wherein Nu: is selected from the group consisting of secondary amino, hydroxyl, and sulfhydryl.

29. The process of claim 1, wherein the Bronsted acid is selected from the group consisting of acids having a $pK_a$ less than about 5 and combinations thereof.

30. The process of claim 29, wherein the Bronsted acid is an inorganic acid.

31. The process of claim 30, wherein the Bronsted acid is selected from the group consisting of hydrochloric acid, hydrobromic acid, sulfuric acid, sulfurous acid, nitric acid, nitrous acid, perchloric acid, phosphoric acid, chromic acid, and combinations thereof.

32. The process of claim 29, wherein the Bronsted acid is an organic acid.

33. The process of claim 32, wherein the organic acid is selected from the group consisting of: carboxylic acids; sulfonic acids; phosphonic acids; and phenols substituted with 1 to 5 electron-withdrawing substituents.

34. The process of claim 33, wherein the organic acid is selected from the group consisting of acetic acid, propionic acid, glycolic acid, pyruvic acid, oxalic acid, malic acid, malonic acid, succinic acid, maleic acid, fumaric acid, tartaric acid, citric acid, benzoic acid, 2-nitrobenzoic acid, cinnamic acid, mandelic acid, methanesulfonic acid, ethanesulfonic acid, triflic acid, p-toluenesulfonic acid, salicylic acid, chloroacetic acid, dichloroacetic acid, trichloroacetic acid, trifluoroacetic acid, and combinations thereof.

35. The process of claim 1, wherein the catalyst is covalently bound, directly or indirectly, to a solid support.

* * * * *